(12) United States Patent
McLaughlin et al.

(10) Patent No.: US 10,130,489 B2
(45) Date of Patent: Nov. 20, 2018

(54) EXPANDABLE VERTEBRAL IMPLANT

(71) Applicant: GLOBUS MEDICAL, INC, Audubon, PA (US)

(72) Inventors: Colm McLaughlin, Glenside, PA (US); George Howard, Green Lane, PA (US); Jason Gray, East Greenville, PA (US); James Himmelberger, Souderton, PA (US)

(73) Assignee: Globus Medical, Inc., Audubon, PA (US)

( * ) Notice: Subject to any disclaimer, the term of this patent is extended or adjusted under 35 U.S.C. 154(b) by 7 days.

(21) Appl. No.: 15/058,186

(22) Filed: Mar. 2, 2016

(65) Prior Publication Data
US 2016/0199192 A1     Jul. 14, 2016

Related U.S. Application Data

(63) Continuation of application No. 14/313,623, filed on Jun. 24, 2014, now Pat. No. 9,301,850, which is a
(Continued)

(51) Int. Cl.
*A61F 2/44*     (2006.01)
*A61F 2/30*     (2006.01)
(Continued)

(52) U.S. Cl.
CPC ............... *A61F 2/446* (2013.01); *A61F 2/44* (2013.01); *A61F 2/4455* (2013.01); *A61F 2/4611* (2013.01); *A61F 2002/2817* (2013.01); *A61F 2002/2835* (2013.01); *A61F 2002/3055* (2013.01); *A61F 2002/30224* (2013.01); *A61F 2002/30383* (2013.01); *A61F 2002/30393* (2013.01); *A61F 2002/30395* (2013.01); *A61F 2002/30405* (2013.01);
(Continued)

(58) Field of Classification Search
CPC ................ A61F 2002/30617; A61F 2/44–2/46
See application file for complete search history.

(56) References Cited

U.S. PATENT DOCUMENTS 3,741,205 A    6/1973   Markolf et al.
3,741,251 A    6/1973   Rees
(Continued)

FOREIGN PATENT DOCUMENTS

DE       4012622 C1     7/1991
DE       4327054 C1     4/1995
(Continued)

*Primary Examiner* — Jacqueline Johanas

(57) ABSTRACT

An expandable implant for engagement between vertebrae includes an inner member, an outer member, and a gear member positioned coaxial with respect to each other such that the inner and outer members are moveable relative to each other along an axis. The inner member includes a longitudinal groove configured to engage a pin extending through the outer member such that the pin prevents the inner member from translating completely through the outer member and aids in alignment and limits rotation of the second endplate. Portions of the implant may be provided with a series of markings such that when the markings are aligned, the implant is aligned in a specific configuration and for a specific implantation approach.

16 Claims, 14 Drawing Sheets

Related U.S. Application Data continuation-in-part of application No. 13/048,604, filed on Mar. 15, 2011, now Pat. No. 9,579,211, which is a continuation-in-part of application No. 12/758,529, filed on Apr. 12, 2010, now Pat. No. 8,282,683.

(51) Int. Cl.
 *A61F 2/46* (2006.01)
 *A61F 2/28* (2006.01)

(52) U.S. Cl.
 CPC .............. *A61F 2002/30484* (2013.01); *A61F 2002/30492* (2013.01); *A61F 2002/30495* (2013.01); *A61F 2002/30523* (2013.01); *A61F 2002/30576* (2013.01); *A61F 2002/30579* (2013.01); *A61F 2002/30594* (2013.01); *A61F 2002/30598* (2013.01); *A61F 2002/30601* (2013.01); *A61F 2002/30617* (2013.01); *A61F 2002/30858* (2013.01); *A61F 2002/4475* (2013.01); *A61F 2002/4625* (2013.01); *A61F 2002/4627* (2013.01); *A61F 2002/4629* (2013.01); *A61F 2310/00011* (2013.01); *A61F 2310/00023* (2013.01); *A61F 2310/00131* (2013.01)

(56) References Cited

U.S. PATENT DOCUMENTS

| | | |
|---|---|---|
| 4,126,338 A | 11/1978 | Coel et al. |
| 4,156,296 A | 5/1979 | Johnson et al. |
| 4,289,123 A | 9/1981 | Dunn |
| 4,309,777 A | 1/1982 | Patil |
| 4,341,482 A | 7/1982 | Wollensak |
| 4,349,921 A | 9/1982 | Kuntz |
| 4,401,112 A | 8/1983 | Rezaian |
| 4,512,038 A | 4/1985 | Alexander et al. |
| 4,545,374 A | 10/1985 | Jacobson |
| 4,553,273 A | 11/1985 | Wu |
| 4,554,914 A | 11/1985 | Kapp et al. |
| 4,599,086 A | 7/1986 | Doty |
| 4,611,581 A | 9/1986 | Steffee |
| 4,636,217 A | 1/1987 | Ogilvie et al. |
| 4,645,503 A | 2/1987 | Lin et al. |
| 4,657,550 A | 4/1987 | Daher |
| 4,696,290 A | 9/1987 | Steffee |
| 4,792,320 A | 12/1988 | Nickel |
| 4,820,305 A | 4/1989 | Harms et al. |
| 4,834,757 A | 5/1989 | Brantigan |
| 4,863,476 A | 9/1989 | Shepperd |
| 4,863,477 A | 9/1989 | Monson |
| 4,878,915 A | 11/1989 | Brantigan |
| 4,892,546 A | 1/1990 | Kotz et al. |
| 4,903,690 A | 2/1990 | Campbell |
| 4,911,718 A | 3/1990 | Lee et al. |
| 4,932,975 A | 6/1990 | Main et al. |
| 4,936,848 A | 6/1990 | Bagby |
| 4,945,127 A | 7/1990 | Kagawa et al. |
| 4,950,258 A | 8/1990 | Kawai et al. |
| 4,950,269 A | 8/1990 | Gaines, Jr. |
| 5,015,247 A | 5/1991 | Michelson |
| 5,019,108 A | 5/1991 | Berlin et al. |
| 5,057,109 A | 10/1991 | Olerud |
| 5,059,193 A | 10/1991 | Kuslich |
| 5,062,850 A | 11/1991 | MacMillan et al. |
| 5,108,395 A | 4/1992 | Laurain |
| 5,123,926 A | 6/1992 | Pisharodi |
| 5,145,935 A | 9/1992 | Hayashi |
| 5,147,404 A | 9/1992 | Downey |
| 5,171,278 A | 12/1992 | Pisharodi |
| 5,171,280 A | 12/1992 | Baumgartner |
| 5,189,110 A | 2/1993 | Ikematu et al. |
| 5,192,326 A | 3/1993 | Bao et al. |
| 5,192,327 A | 3/1993 | Brantigan |
| 5,209,732 A | 5/1993 | Lampropoulos et al. |
| 5,234,378 A | 8/1993 | Helgesen et al. |
| 5,236,460 A | 8/1993 | Barber |
| 5,263,953 A | 11/1993 | Bagby |
| 5,290,289 A | 3/1994 | Sanders et al. |
| 5,290,312 A | 3/1994 | Kojimoto et al. |
| 5,306,310 A | 4/1994 | Siebels |
| 5,330,535 A | 7/1994 | Moser et al. |
| 5,336,223 A | 8/1994 | Rogers |
| 5,364,397 A | 11/1994 | Hayes et al. |
| 5,375,823 A | 12/1994 | Navas |
| 5,382,226 A | 1/1995 | Graham |
| 5,390,683 A | 2/1995 | Pisharodi |
| 5,443,515 A | 8/1995 | Cohen et al. |
| 5,458,641 A | 10/1995 | Ramirez |
| 5,489,308 A | 2/1996 | Kuslich et al. |
| 5,496,216 A | 3/1996 | Rohrle et al. |
| 5,522,899 A | 6/1996 | Michelson |
| 5,534,028 A | 7/1996 | Bao et al. |
| 5,534,029 A | 7/1996 | Shima |
| 5,534,030 A | 7/1996 | Navarro et al. |
| 5,540,689 A | 7/1996 | Sanders et al. |
| 5,549,679 A | 8/1996 | Kuslich |
| 5,554,191 A | 9/1996 | Lahille et al. |
| 5,562,736 A | 10/1996 | Kay et al. |
| 5,569,176 A | 10/1996 | Graham |
| 5,571,190 A | 11/1996 | Ulrich |
| 5,571,192 A | 11/1996 | Schonhoffer |
| 5,601,493 A | 2/1997 | Nakazono et al. |
| 5,603,713 A | 2/1997 | Aust et al. |
| 5,603,722 A | 2/1997 | Phan et al. |
| 5,607,474 A | 3/1997 | Athanasiou et al. |
| 5,645,596 A | 7/1997 | Kim |
| 5,653,763 A | 8/1997 | Errico et al. |
| 5,665,122 A | 9/1997 | Kambin |
| 5,674,286 A | 10/1997 | D'Alessio et al. |
| 5,674,295 A | 10/1997 | Ray et al. |
| 5,676,699 A | 10/1997 | Gogolewski et al. |
| 5,676,701 A | 10/1997 | Yuan et al. |
| 5,683,465 A | 11/1997 | Shinn et al. |
| 5,693,100 A | 12/1997 | Pisharodi |
| 5,702,453 A | 12/1997 | Rabbe et al. |
| 5,702,455 A | 12/1997 | Saggar |
| 5,713,841 A | 2/1998 | Graham |
| 5,716,410 A | 2/1998 | Wang et al. |
| 5,716,416 A | 2/1998 | Lin |
| 5,723,013 A | 3/1998 | Jeanson et al. |
| 5,749,916 A | 5/1998 | Richelsoph |
| 5,771,835 A * | 6/1998 | Schneider .............. G09F 11/23 116/209 |
| 5,776,197 A | 7/1998 | Rabbe et al. |
| 5,776,198 A | 7/1998 | Rabbe et al. |
| 5,800,433 A | 9/1998 | Benzel et al. |
| 5,824,093 A | 10/1998 | Ray et al. |
| 5,836,948 A | 11/1998 | Zucherman et al. |
| 5,843,082 A | 12/1998 | Yuan et al. |
| 5,860,977 A | 1/1999 | Zucherman et al. |
| 5,861,035 A | 1/1999 | Griffith |
| 5,863,297 A | 1/1999 | Walter et al. |
| 5,868,745 A | 2/1999 | Alleyne |
| 5,868,746 A | 2/1999 | Sarver et al. |
| 5,876,404 A | 3/1999 | Zucherman et al. |
| 5,888,220 A | 3/1999 | Felt et al. |
| 5,888,224 A | 3/1999 | Beckers et al. |
| 5,895,428 A | 4/1999 | Berry |
| 5,899,904 A | 5/1999 | Errico et al. |
| 5,899,905 A | 5/1999 | Lemperle et al. |
| 5,954,744 A | 9/1999 | Phan et al. |
| 5,964,760 A | 10/1999 | Richelsoph |
| 5,976,186 A | 11/1999 | Bao et al. |
| 5,976,187 A | 11/1999 | Richelsoph |
| 5,980,522 A | 11/1999 | Koros et al. |
| 5,980,572 A | 11/1999 | Kim et al. |
| 5,984,967 A | 11/1999 | Zdeblick et al. |
| 5,989,290 A | 11/1999 | Biedermann et al. |
| 5,989,291 A | 11/1999 | Ralph et al. |
| 6,010,290 A | 1/2000 | Slesinski et al. |
| 6,015,436 A | 1/2000 | Schonhoffer |
| 6,017,345 A | 1/2000 | Richelsoph |

(56) References Cited

U.S. PATENT DOCUMENTS

| | | |
|---|---|---|
| 6,017,366 A | 1/2000 | Berman |
| 6,019,793 A | 2/2000 | Perren et al. |
| 6,022,352 A | 2/2000 | Vandewalle |
| 6,024,764 A | 2/2000 | Schroeppel |
| 6,036,693 A | 3/2000 | Yuan et al. |
| 6,039,761 A | 3/2000 | Li et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,071,982 A | 6/2000 | Wise et al. |
| 6,074,390 A | 6/2000 | Zucherman et al. |
| 6,080,193 A | 6/2000 | Hochschuler et al. |
| 6,086,613 A | 7/2000 | Camino et al. |
| 6,090,112 A | 7/2000 | Zucherman et al. |
| 6,090,996 A | 7/2000 | Li |
| 6,093,205 A | 7/2000 | McLeod et al. |
| 6,099,531 A | 8/2000 | Bonutti |
| 6,102,932 A | 8/2000 | Kurz |
| 6,102,933 A | 8/2000 | Lee et al. |
| 6,126,689 A | 10/2000 | Brett |
| 6,127,597 A | 10/2000 | Beyar et al. |
| 6,132,432 A | 10/2000 | Richelsoph |
| 6,132,465 A | 10/2000 | Ray et al. |
| 6,136,031 A | 10/2000 | Middleton |
| 6,149,652 A | 11/2000 | Zucherman et al. |
| 6,152,926 A | 11/2000 | Zucherman et al. |
| 6,156,038 A | 12/2000 | Zucherman et al. |
| 6,156,842 A | 12/2000 | Hoenig et al. |
| 6,159,244 A | 12/2000 | Suddaby |
| 6,160,084 A | 12/2000 | Langer et al. |
| 6,174,334 B1 | 1/2001 | Suddaby |
| 6,176,881 B1 | 1/2001 | Schar et al. |
| 6,176,882 B1 | 1/2001 | Biedermann et al. |
| 6,179,873 B1 | 1/2001 | Zientek |
| 6,183,471 B1 | 2/2001 | Zucherman et al. |
| 6,187,048 B1 | 2/2001 | Milner et al. |
| 6,190,387 B1 | 2/2001 | Zucherman et al. |
| 6,193,720 B1 | 2/2001 | Yuan et al. |
| 6,193,757 B1 | 2/2001 | Foley et al. |
| 6,200,322 B1 | 3/2001 | Branch et al. |
| 6,206,883 B1 | 3/2001 | Tunc |
| 6,206,923 B1 | 3/2001 | Boyd et al. |
| 6,214,005 B1 | 4/2001 | Benzel et al. |
| 6,217,579 B1 | 4/2001 | Koros |
| 6,221,075 B1 | 4/2001 | Tormala et al. |
| 6,235,030 B1 | 5/2001 | Zucherman et al. |
| 6,238,397 B1 | 5/2001 | Zucherman et al. |
| 6,248,131 B1 | 6/2001 | Felt et al. |
| 6,258,125 B1 | 7/2001 | Paul et al. |
| 6,261,289 B1 | 7/2001 | Levy |
| 6,264,695 B1 | 7/2001 | Stoy |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,344,057 B1 | 2/2002 | Rabbe et al. |
| 6,358,254 B1 | 3/2002 | Anderson |
| 6,368,351 B1 | 4/2002 | Glenn et al. |
| 6,375,682 B1 | 4/2002 | Fleischmann et al. |
| 6,379,355 B1 | 4/2002 | Zucherman et al. |
| 6,395,031 B1 | 5/2002 | Foley et al. |
| 6,402,750 B1 | 6/2002 | Atkinson et al. |
| 6,409,766 B1 | 6/2002 | Brett |
| 6,419,676 B1 | 7/2002 | Zucherman et al. |
| 6,419,677 B2 | 7/2002 | Zucherman et al. |
| 6,425,919 B1 | 7/2002 | Lambrecht |
| 6,428,544 B1 | 8/2002 | Ralph et al. |
| 6,436,102 B1 | 8/2002 | Ralph et al. |
| 6,436,140 B1 | 8/2002 | Liu et al. |
| 6,436,143 B1 | 8/2002 | Ross et al. |
| 6,443,989 B1 | 9/2002 | Jackson |
| 6,451,019 B1 | 9/2002 | Zucherman et al. |
| 6,451,020 B1 | 9/2002 | Zucherman et al. |
| 6,451,057 B1 | 9/2002 | Chen et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,468,310 B1 | 10/2002 | Ralph et al. |
| 6,471,725 B1 | 10/2002 | Ralph et al. |
| 6,478,796 B2 | 11/2002 | Zuckerman et al. |
| 6,482,234 B1 | 11/2002 | Weber et al. |
| 6,482,235 B1 | 11/2002 | Lambrecht et al. |
| 6,485,517 B1 | 11/2002 | Michelson |
| 6,488,682 B2 | 12/2002 | Kikuchi et al. |
| 6,488,683 B2 | 12/2002 | Lieberman |
| 6,488,710 B2 | 12/2002 | Besselink |
| 6,491,724 B1 | 12/2002 | Ferree |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,514,256 B2 | 2/2003 | Zucherman et al. |
| 6,520,991 B2 | 2/2003 | Huene |
| 6,524,341 B2 | 2/2003 | Lang et al. |
| 6,527,806 B2 | 3/2003 | Ralph et al. |
| 6,551,319 B2 | 4/2003 | Lieberman |
| 6,551,320 B2 | 4/2003 | Lieberman |
| 6,558,390 B2 | 5/2003 | Cragg |
| 6,562,074 B2 | 5/2003 | Gerbec et al. |
| 6,576,016 B1 | 6/2003 | Hochschuler et al. |
| 6,582,467 B1 | 6/2003 | Teitelbaum et al. |
| 6,554,863 B2 | 8/2003 | Paul et al. |
| 6,607,559 B2 | 8/2003 | Ralph et al. |
| 6,613,089 B1 | 9/2003 | Estes et al. |
| 6,641,614 B1 | 11/2003 | Wagner et al. |
| 6,648,917 B2 | 11/2003 | Gerbec et al. |
| 6,652,584 B2 | 11/2003 | Michelson |
| 6,660,038 B2 | 12/2003 | Boyer, II et al. |
| 6,666,891 B2 | 12/2003 | Boehm et al. |
| 6,692,495 B1 | 2/2004 | Zacouto |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,852 B1 | 3/2004 | Chung et al. |
| 6,716,216 B1 | 4/2004 | Boucher et al. |
| 6,716,247 B2 | 4/2004 | Michelson |
| 6,719,796 B2 | 4/2004 | Cohen et al. |
| 6,723,126 B1 | 4/2004 | Berry |
| 6,730,088 B2 | 5/2004 | Yeh |
| 6,730,126 B2 | 5/2004 | Boehm, Jr. et al. |
| 6,733,534 B2 | 5/2004 | Sherman |
| 6,740,119 B2 | 5/2004 | Ralph et al. |
| 6,743,255 B2 | 6/2004 | Ferree |
| 6,749,386 B2 | 6/2004 | Harris |
| 6,749,614 B2 | 6/2004 | Teitelbaum et al. |
| 6,752,832 B2 | 6/2004 | Neumann |
| 6,758,861 B2 | 7/2004 | Ralph et al. |
| 6,758,863 B2 | 7/2004 | Estes et al. |
| 6,764,491 B2 | 7/2004 | Frey et al. |
| 6,764,515 B2 | 7/2004 | Ralph et al. |
| 6,773,460 B2 | 8/2004 | Jackson |
| 6,776,781 B1 | 8/2004 | Uwaydah |
| 6,830,589 B2 | 12/2004 | Erickson |
| 6,835,159 B2 | 12/2004 | Gehring et al. |
| 6,849,093 B2 | 2/2005 | Michelson |
| 6,852,129 B2 | 2/2005 | Gerbec et al. |
| 6,863,673 B2 | 3/2005 | Gerbec et al. |
| 6,866,682 B1 | 3/2005 | An et al. |
| 6,881,228 B2 | 4/2005 | Zdeblick et al. |
| 6,972,019 B2 | 12/2005 | Michelson |
| 6,976,816 B2 | 12/2005 | Slesinski et al. |
| 7,018,415 B1 | 3/2006 | McKay |
| 7,056,343 B2 | 6/2006 | Schafer et al. |
| 7,070,598 B2 | 7/2006 | Lim et al. |
| 7,077,864 B2 | 7/2006 | Byrd, III |
| 7,135,043 B2 | 11/2006 | Nakahara |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,442,209 B2 | 10/2008 | Michelson |
| 7,473,276 B2 | 1/2009 | Aebi et al. |
| 7,544,208 B1 | 6/2009 | Mueller et al. |
| 7,547,325 B2 | 6/2009 | Biedermann et al. |

(56) References Cited

U.S. PATENT DOCUMENTS

| | | |
|---|---|---|
| 7,588,573 B2 | 9/2009 | Berry |
| 7,621,953 B2 | 11/2009 | Braddock, Jr. et al. |
| 7,641,693 B2 | 1/2010 | Gütlin |
| 7,674,296 B2 | 3/2010 | Rhoda |
| 7,682,396 B2 | 3/2010 | Beaurain et al. |
| 7,691,147 B2 | 4/2010 | Gitlin |
| 7,749,270 B2 | 7/2010 | Peterman |
| 7,753,958 B2 | 7/2010 | Gordon |
| 7,758,648 B2 | 7/2010 | Castleman |
| 7,771,473 B2 | 8/2010 | Thramann |
| 7,780,732 B2 | 8/2010 | Abernathie |
| 7,794,502 B2 | 9/2010 | Michelson |
| 7,799,081 B2 | 9/2010 | McKinley |
| 7,811,327 B2 | 10/2010 | Hansell |
| 7,815,683 B2 | 10/2010 | Melkent et al. |
| 7,837,734 B2 | 11/2010 | Zucherman et al. |
| 7,846,207 B2 | 12/2010 | Lechmann |
| 7,862,616 B2 | 1/2011 | Lechmann |
| 7,875,078 B2 | 1/2011 | Wysocki et al. |
| 7,879,096 B2 | 2/2011 | Dickson |
| 7,901,409 B2 | 3/2011 | Canaveral et al. |
| 7,909,869 B2 | 3/2011 | Gordon et al. |
| 7,909,870 B2 | 3/2011 | Kraus |
| 7,914,581 B2 | 3/2011 | Dickson |
| 7,972,363 B2 | 7/2011 | Moskowitz |
| 7,985,255 B2 | 7/2011 | Bray |
| 8,034,111 B2 | 10/2011 | Hsu |
| 8,123,810 B2 | 2/2012 | Gordon et al. |
| 8,152,851 B2 | 4/2012 | Mueller et al. |
| 8,161,619 B2 | 4/2012 | Wanthal |
| 8,430,759 B2 | 4/2013 | Wanthal |
| 8,647,386 B2 | 2/2014 | Gordon et al. |
| 8,721,723 B2 | 5/2014 | Hansell et al. |
| 9,301,850 B2* | 4/2016 | McLaughlin .............. A61F 2/44 |
| 2002/0045945 A1 | 4/2002 | Liu |
| 2004/0049271 A1 | 3/2004 | Biedermann |
| 2004/0054412 A1 | 3/2004 | Gerbec et al. |
| 2004/0153065 A1 | 8/2004 | Lim |
| 2004/0172129 A1 | 9/2004 | Schafer et al. |
| 2004/0181283 A1 | 9/2004 | Boyer, II et al. |
| 2004/0193272 A1 | 9/2004 | Zubok et al. |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0281613 A1 | 12/2005 | Tella et al. |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0058877 A1 | 3/2006 | Gutlin |
| 2006/0058878 A1 | 3/2006 | Michelson |
| 2006/0085071 A1 | 4/2006 | Lechmann et al. |
| 2006/0100710 A1 | 5/2006 | Gutlin et al. |
| 2006/0122701 A1 | 6/2006 | Kister |
| 2006/0129241 A1* | 6/2006 | Boyer, II .............. B29C 43/006 623/17.15 |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241762 A1 | 10/2006 | Kraus |
| 2006/0241763 A1 | 10/2006 | Paul et al. |
| 2006/0241770 A1 | 10/2006 | Rhoda et al. |
| 2006/0253201 A1 | 11/2006 | Mcluen |
| 2007/0028710 A1 | 2/2007 | Kraus et al. |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0191954 A1 | 8/2007 | Hansell et al. |
| 2007/0250171 A1 | 10/2007 | Bonin, Jr. |
| 2007/0255407 A1 | 11/2007 | Castleman et al. |
| 2007/0255410 A1 | 11/2007 | Dickson et al. |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0015704 A1 | 1/2008 | Gradl et al. |
| 2008/0021559 A1 | 1/2008 | Thramann |
| 2008/0065222 A1 | 3/2008 | Hamada |
| 2008/0140207 A1 | 6/2008 | Olmos et al. |
| 2008/0167657 A1 | 7/2008 | Greenhalgh |
| 2008/0183204 A1 | 7/2008 | Greenhalgh et al. |
| 2008/0183293 A1 | 7/2008 | Parry |
| 2008/0243254 A1 | 10/2008 | Butler |
| 2008/0275455 A1 | 11/2008 | Berry et al. |
| 2008/0281346 A1 | 11/2008 | Greenhalgh et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0043393 A1 | 2/2009 | Duggal et al. |
| 2009/0088853 A1 | 4/2009 | Ogilvie et al. |
| 2009/0112320 A1 | 4/2009 | Kraus |
| 2009/0112324 A1 | 4/2009 | Refai |
| 2009/0112325 A1 | 4/2009 | Refai |
| 2009/0125062 A1 | 5/2009 | Arnin |
| 2009/0138089 A1* | 5/2009 | Doubler .................... A61F 2/44 623/17.16 |
| 2009/0149956 A1 | 6/2009 | Greenhalgh et al. |
| 2009/0149959 A1 | 6/2009 | Conner et al. |
| 2009/0164019 A1 | 6/2009 | Hsu et al. |
| 2009/0182430 A1 | 7/2009 | Tyber |
| 2009/0192613 A1 | 7/2009 | Wing |
| 2009/0204218 A1 | 8/2009 | Richelsoph |
| 2009/0222100 A1 | 9/2009 | Cipoletti et al. |
| 2009/0234455 A1 | 9/2009 | Moskowitz |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070029 A1 | 3/2010 | Drews et al. |
| 2010/0070041 A1 | 3/2010 | Peterman |
| 2010/0082109 A1 | 4/2010 | Greenhalgh et al. |
| 2010/0094424 A1 | 4/2010 | Woodburn et al. |
| 2010/0106251 A1 | 4/2010 | Kast |
| 2010/0145460 A1 | 6/2010 | Mcdonough |
| 2010/0179655 A1 | 7/2010 | Hansell et al. |
| 2010/0179657 A1 | 7/2010 | Greenhalgh et al. |
| 2010/0185297 A1 | 7/2010 | Steinberg |
| 2010/0274357 A1 | 10/2010 | Miller et al. |
| 2010/0280614 A1 | 11/2010 | Castleman |
| 2010/0298942 A1 | 11/2010 | Hansell |
| 2011/0087328 A1 | 4/2011 | Dickson |
| 2011/0097174 A1 | 4/2011 | Varden |
| 2011/0178598 A1 | 7/2011 | Rhoda |
| 2011/0184424 A1 | 7/2011 | Isch et al. |
| 2011/0184524 A1 | 7/2011 | Wiedenbeck |
| 2011/0196493 A1 | 8/2011 | Pimenta |
| 2011/0218631 A1 | 9/2011 | Woodburn, Sr. et al. |
| 2011/0251691 A1* | 10/2011 | McLaughlin .............. A61F 2/44 623/17.16 |
| 2011/0251692 A1* | 10/2011 | McLaughlin .............. A61F 2/44 623/17.16 |
| 2012/0130493 A1 | 5/2012 | McLaughlin et al. |
| 2012/0179255 A1* | 7/2012 | DeFalco .................... A61F 2/44 623/17.11 |
| 2012/0209384 A1 | 8/2012 | Arnold et al. |
| 2012/0265303 A1 | 10/2012 | Refai et al. |
| 2013/0030536 A1 | 1/2013 | Rhoda et al. |
| 2013/0150971 A1* | 6/2013 | DeFalco .................... A61F 2/44 623/17.16 |

(56) References Cited

U.S. PATENT DOCUMENTS

| | | | |
|---|---|---|---|
| 2013/0331943 A1* | 12/2013 | Arnold | A61F 2/4455 |
| | | | 623/17.15 |
| 2014/0156006 A1* | 6/2014 | Bannigan | A61F 2/44 |
| | | | 623/17.15 |
| 2014/0205969 A1* | 7/2014 | Marlin | A61C 8/0001 |
| | | | 433/173 |
| 2015/0018957 A1 | 1/2015 | Nichols et al. | |
| 2015/0282948 A1* | 10/2015 | Arnold | A61F 2/4455 |
| | | | 623/17.16 |
| 2016/0193050 A1* | 7/2016 | Cappelletti | A61F 2/3609 |
| | | | 623/18.11 |
| 2016/0287395 A1* | 10/2016 | Khalili | A61F 2/30942 |

FOREIGN PATENT DOCUMENTS

| | | |
|---|---|---|
| EP | 0576379 B1 | 6/1993 |
| EP | 0610837 B1 | 7/1994 |
| SU | 1424826 A1 | 9/1988 |
| WO | 9201428 A1 | 2/1992 |
| WO | 9525485 A1 | 9/1995 |
| WO | 2004096103 A1 | 11/2004 |

\* cited by examiner

EXPANDABLE VERTEBRAL IMPLANT

CROSS-REFERENCE TO RELATED APPLICATIONS

The present application is a continuation of U.S. patent application Ser. No. 14/313,623, filed Jun. 24, 2014, which is a continuation-in-part of U.S. patent application Ser. No. 13/048,604, filed Mar. 15, 2011, which is a continuation-in-part of U.S. patent application Ser. No. 12/758,529, filed on Apr. 12, 2010, now U.S. Pat. No. 8,282,683, the entire disclosures of which are incorporated herein by reference in their entireties for all purposes.

FIELD OF THE INVENTION

The present invention relates to a device to support the spine after removal of at least a part of a vertebra. In particular, the device may be in the form of a multi-level implant which can replace multiple vertebral bodies.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit by in vivo expansion of the device. Some other advantages offered by an expandable prosthetic device are that they can facilitate distraction across the resected vertebral defect and allow immediate load bearing after corpectomy.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

According to one embodiment, an expandable prosthetic implant for engagement between vertebrae includes an inner member, a first endplate, an outer member, at least one pin, a gear member, and a second endplate. The inner member has a hollow interior portion and an external portion and includes a longitudinal groove extending along a length of the inner member. The first endplate is configured to engage a first vertebral body and is connected to the inner member. The outer member has a hollow interior portion configured to coaxially receive the inner member therein. The inner and outer members are moveable relative to each other along a longitudinal axis. The pin has a first end and a second end and the pin extends through the outer member such that the second end is configured to engage the groove in the inner member. The gear member is positioned coaxial to the inner member and outer member and axially fixed to the outer member. The second endplate is configured to engage a second vertebral body and is connected to the outer member.

The pin may protrude from an outer surface and/or an inner surface of the outer member. The pin may be configured to fit between a plurality tabs on a distal end of the second endplate to aid in alignment and limit rotation of the second endplate. The pin may engage with an uppermost surface of the groove to prevent the inner member from translating through an opening in a proximal end of the outer member. The pin may be fixed to the outer member. The pin may be positioned transversely to the outer member. The inner member may include a second groove configured to receive a second pin protruding from the outer member.

According to another embodiment, an expandable prosthetic implant for engagement between vertebrae includes an inner member having a hollow interior portion and an external portion. A first endplate configured to engage a first vertebral body is connected to the inner member and the first endplate includes a first series of markings. An outer member having a hollow interior portion is configured to coaxially receive the inner member therein. The inner and outer members are moveable relative to each other along a longitudinal axis. A gear member is positioned coaxial to the inner member and outer member and axially fixed to the outer member. A second endplate configured to engage a second vertebral body is connected to the outer member and the second endplate includes a second series of markings. When at least one of the first and second series of markings are aligned, the first and second endplates are aligned for a specific approach (e.g., anterior, etc.).

The first and second series of markings may include, for example, alphanumeric characters, numeric characters, colors, symbols, shapes, words, or pictures. The first series of markings may include a plurality of different markings. The first series of markings may be positioned around a perimeter of an extension portion of the first endplate. The second series of markings may include a plurality of different markings which correspond to the first series of markings. The second series of markings may be positioned around a perimeter of the second endplate proximate to a plurality of tabs that connect the second endplate to the outer member. A third marking may be provided on the inner or outer members to aid in alignment of all of the components of the implant.

The implant may also include a locking member configured to restrict relative movement between the inner member and the outer member. The locking member may be configured to be received in the outer member. The locking member may include an engagement member that engages the gear member to prevent rotation of the gear member. The engagement member may engage a cutout formed in the gear member to prevent rotation of the gear member. The gear member may include gear teeth extending around a perimeter of the gear member. The gear teeth may extend from a proximal end of the gear member to a distal end of the gear member.

According to another embodiment, an expandable prosthetic implant for engagement between vertebrae includes an inner member having a hollow interior portion and an external portion and the inner member includes a longitudinal groove extending along a length of the inner member. A first endplate is configured to engage a first vertebral body and is connected to the inner member. The first endplate includes a first series of markings. An outer member having a hollow interior portion is configured to coaxially receive the inner member therein. The inner and outer members are moveable relative to each other along a longitudinal axis. A pin having a first end and a second end extends through the outer member. The second end of the pin is configured to engage the groove in the inner member. A second endplate is configured to engage a second vertebral body and is connected to the outer member. The second endplate includes a second series of markings. A gear member is positioned coaxial to the inner member and outer member and axially fixed to the outer member. A locking member is configured to restrict relative movement between the inner member and the outer member. The locking member is configured to be received in the outer member. When at least one of the first and second series of markings are aligned, the first and second endplates are aligned for a specific implantation approach.

According to another embodiment, an expandable prosthetic implant device for engagement between vertebrae generally includes an inner member, outer member, and gear member positioned coaxial with respect to each other such that the inner and outer members are moveable relative to each other along an axis. The inner member has a hollow interior portion and a threaded external portion and includes a first end portion configured to engage an endplate which is capable of engaging a first vertebral body. The outer member has a hollow interior portion configured to receive the inner member and includes a second end portion configured to engage an endplate which is capable of engaging a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes teeth extending around the perimeter of the gear member and the teeth are exposed to the exterior and configured to be accessible by a tool member.

BRIEF DESCRIPTION OF THE DRAWINGS

The present invention will be more readily understood with reference to the embodiments thereof illustrated in the attached drawing figures, in which.

Throughout the drawing figures, it should be understood that like numerals refer to like features and structures.

DETAILED DESCRIPTION OF THE INVENTION

Figure 1:
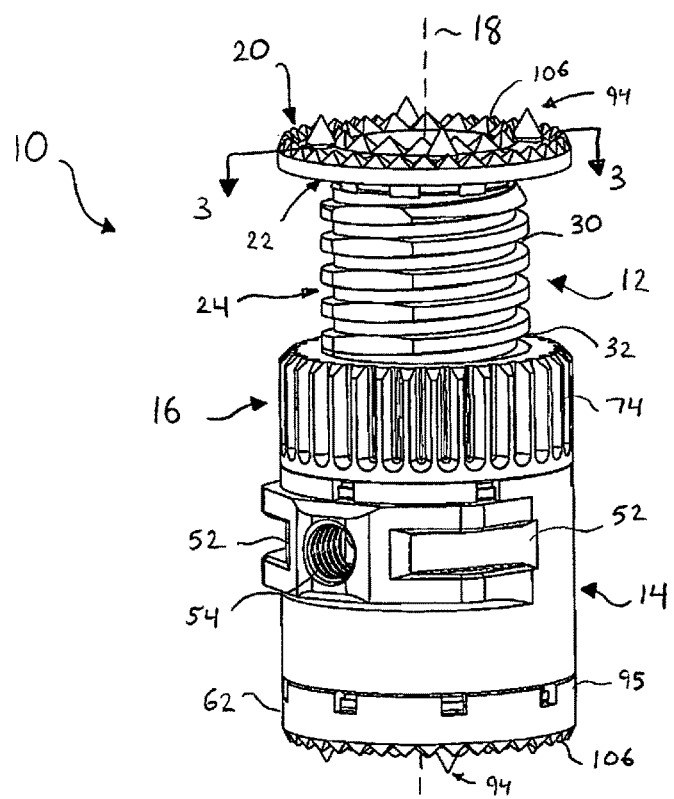
FIG. 1 is a perspective view of an implant in accordance with an embodiment of the present invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose. The features of one embodiment may be employed with other embodiments as the skilled artisan would recognize, even if not explicitly stated herein.

Referring to FIGS. 1-6, a preferred embodiment of an expandable vertebral implant 10 is shown. The implant 10 preferably comprises an inner member 12 which may be telescopingly received within an outer member 14. The implant 10 further comprises a gear member 16 generally configured to effect translation of the inner member 12 with respect to the outer member 14 thereby allowing for expansion and contraction of the implant 10. The inner member 12, the outer member 14, and the gear member 16 are preferably centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-5, the inner member 12 has a generally cylindrical body 24 with a distal end 22 and a proximal end 36. In a preferred embodiment, the body 24 of the inner member 12 comprises an inner surface 28 and an outer surface 30 and generally defines a hollow interior portion 23 extending axially therethrough. At least part of the outer surface 30 preferably includes external threads 32. Located proximate to the distal end 22 of the body 24 are a plurality of tabs 38 which assist in connecting and positionally locating an endplate 20. In a preferred embodiment, the body 24 is configured and dimensioned to be cooperatively received within outer member 14.

Figure 5:
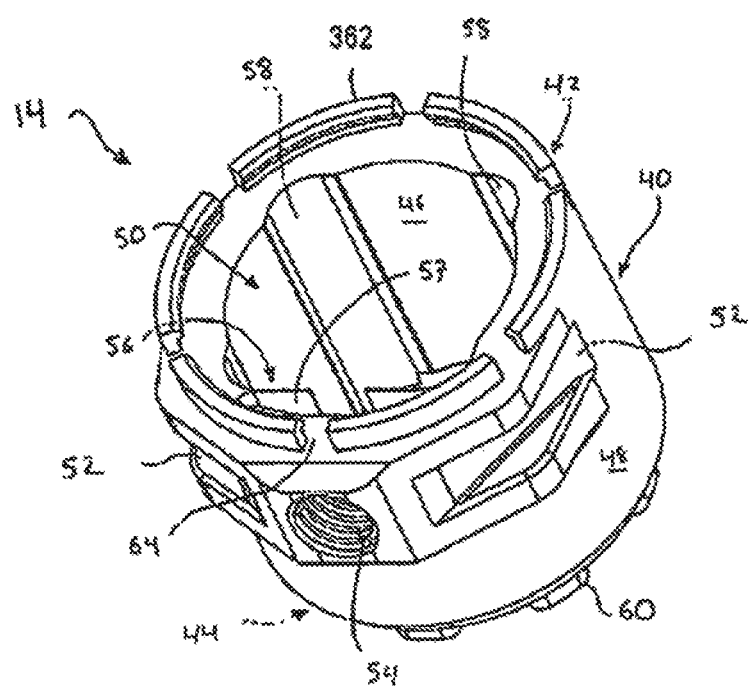
FIG. 5 is perspective view of an embodiment of an outer member of the implant of FIG. 1.

The outer member 14 has a generally cylindrical body 40 with a distal end 42 and a proximal end 44. In a preferred embodiment, the body 40 of the outer member 14 comprises an inner surface 46 and an outer surface 48 and generally defines a hollow interior portion 50 extending axially therethrough. The outer surface 48 preferably has at least one slot 52 and an opening 54 configured and dimensioned to receive a portion of an implantation tool. In a preferred embodiment, the opening 54 extends from the outer surface 48 to the hollow interior portion 50 and at least a portion of the opening 54 is threaded. As best seen in FIG. 5, the inner surface 46 includes a channel 57 for receiving a locking member (discussed below). Located proximate to the proximal end 44 of the outer member 14 are a plurality of tabs 60 which assist in connecting and positionally locating an endplate 62. In a preferred embodiment, a lip 162 is formed around the exterior of the distal end 42 of body 40 and is configured to cooperatively fit with a portion of the gear member 16. A plurality of relief spaces or slots 64 are radially spaced around lip 162 to facilitate a snapping engagement of the lip 162 with the gear member 16. In this regard, slots 64 allow the lip 162 to deform slightly and contract in the radial direction to accommodate gear member 16 to snap on to lip 162. In a preferred embodiment, the interior portion 50 of body 44 is configured and dimensioned to cooperatively receive body 24 of inner member 12 within outer member 14. In this regard, the dimensions of interior portion 50 of body 44 are greater than dimensions of body 24 of inner member 12.

As best seen in FIGS. 2-5, in a preferred embodiment of a prosthetic device 10, the body 24 of the inner member 12 includes a flattened portion 34 which extends at least in part from the distal end 22 to the proximal end 36 and includes a base member 37 having at least one lobe 39 located proximate to the distal end 36 of the body 24. Focusing on FIG. 5, the body 40 of the outer member 14 includes a flattened area 56 and at least one depression 58 on the inner surface 46. When the inner member 12 is assembled within the outer member 14, the flattened area 56 of the outer member 14 cooperatively aligns with the flattened portion 34 of the inner member 12 and the at least one depression 58 of outer member 14 receives the at least one lobe 39 of the inner member 12. The flattened portion 34 and the flattened area 56 along with the lobes 39 and the depressions 58 cooperate to allow the inner member 12 to linearly move with respect to the outer member 14 but prevent the inner member 12 from rotating with respect to the outer member 14. In addition, the base member 37 serves as a stop preventing the inner member 12 from rotating to a point of disengagement from outer member 14.

Figure 6:
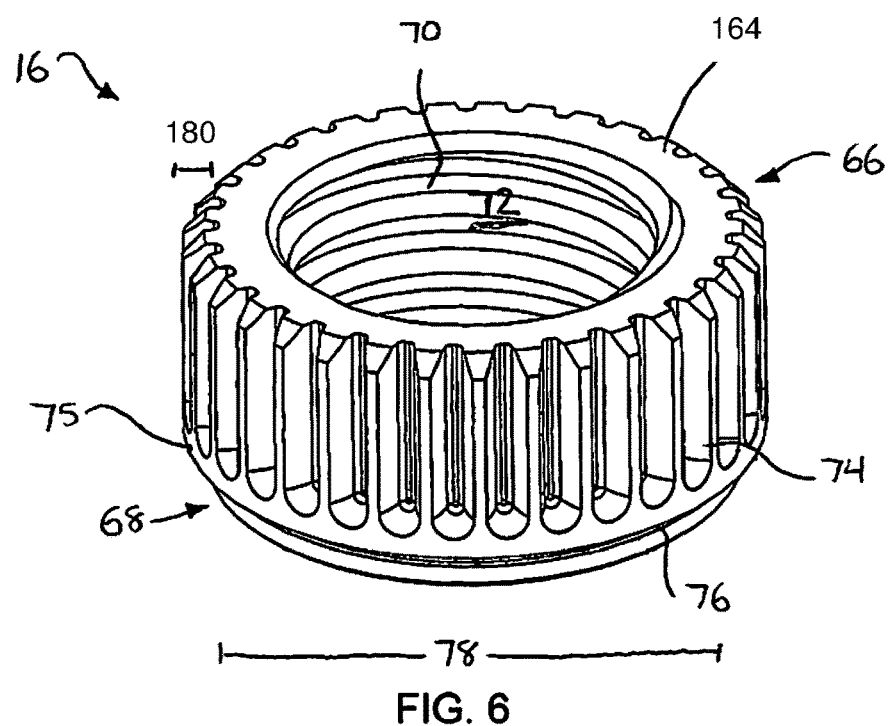
FIG. 6 is an elevated perspective view of one embodiment of a gear member of the implant of FIG. 1.
Figure 7:
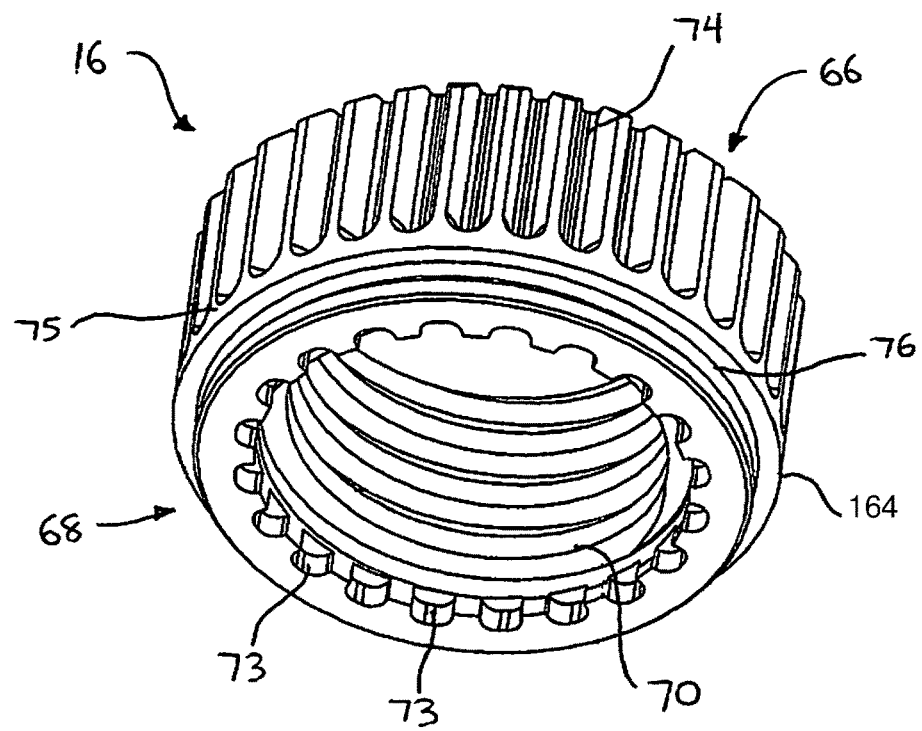
FIG. 7 is a bottom perspective view of the gear member of FIG. 6.

Referring now to FIGS. 6-7, a gear member 16 comprises a generally hollow body 164 extending from a distal end 66 to a proximal end 68 with a helical thread 70 along at least part of an inner wall 72 and an array of gear teeth 74 along a portion of the exterior wall 75. The gear member 16 is generally configured to rotatably connect to the distal end 42 of the outer member 14 and the internal helical thread 70 is configured to engage the external threads 32 of the inner member 12 to cause translation of the inner member 12 with respect to the outer member 14. In a preferred embodiment, the gear member 16 includes a cylindrical cutout feature 76 extending around the inner wall to cooperatively receive the lip 54 of the outer member 14. In this regard, the gear member 16 may rotate freely with respect to the outer member 14 while being retained from longitudinal and lateral movement. In a preferred embodiment, the gear member 16 also includes a series of cutouts 73 located proximate to the proximal end 68 for engaging a portion of a locking member.

With continued reference to FIGS. 6-7, the gear teeth 74 extend substantially from the proximal end 68 to the distal end 66 and extend around the entire periphery of at least a portion of the exterior wall 75. The outer-most external diameter 78 of the gear member 16 is sized to be the same as or slightly smaller than the smallest outer diameter of the endplates 20, 62 and the outer member 14. In this regard, when the implant 10 is viewed from the end in a plane perpendicular to the longitudinal axis 18, the gear member 16 does not protrude radially outward from beyond the perimeter of the endplates 20, 62.

As shown in FIG. 7, in a preferred embodiment, the gear teeth 74 extend a width 180 in a generally radial direction and generally extend radially outward to the outer diameter of the gear member 16. In this regard, the teeth 74 may be designed to have a width 180 to accommodate the expected gear forces given the particular gear ratio, types of material used, and desired overall diameter of prosthetic device 10. One skilled in the art will appreciate that the larger the outer diameter to which the teeth 74 radially extend, the larger the teeth 74 may be designed while still maintaining the same gear ratio. In this regard, when the teeth 74 are made larger, they generally have a better mechanical strength. Also, the ability to design larger, wider, and stronger teeth 74 is advantageous for embodiments where the implant 10 is made of PEEK, other plastic, or other non-metallic materials that may have less mechanical strength than, for instance, titanium.

Furthermore, as described in one embodiment, because the outer-most diameter of the gear member 16 may be as large as the outer diameter of the endplates 20, 62, and the teeth 74 extend radially to the outer-most diameter of the gear member 16, a larger inner diameter of the gear member 16 may be manufactured without compromising mechanical gear strength. As a result, a larger overall inner diameter of the implant 10 may be accommodated which allows the packing of more bone material therein and facilitates bone fusion once the implant 10 is implanted.

Figure 3:
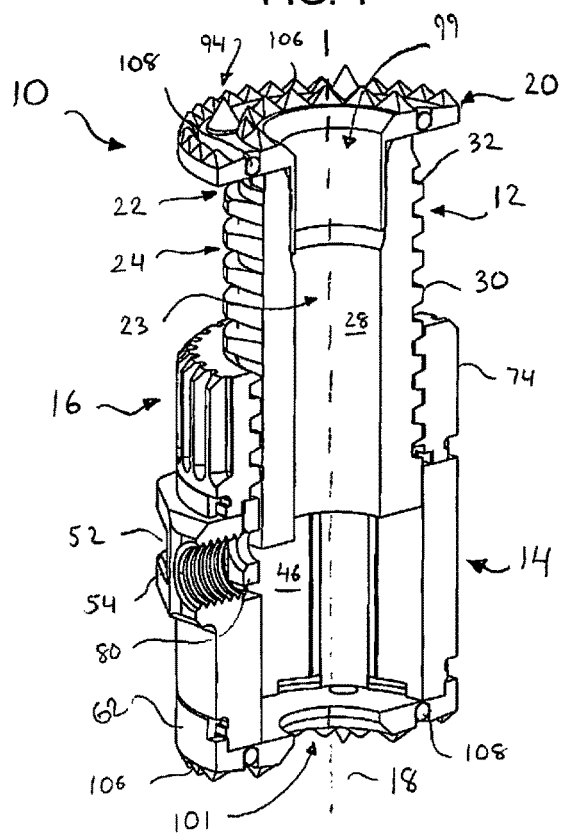
FIG. 3 is a cross-sectional view of the implant of FIG. 1 taken along line 3-3 of FIG. 1.
Figure 2:
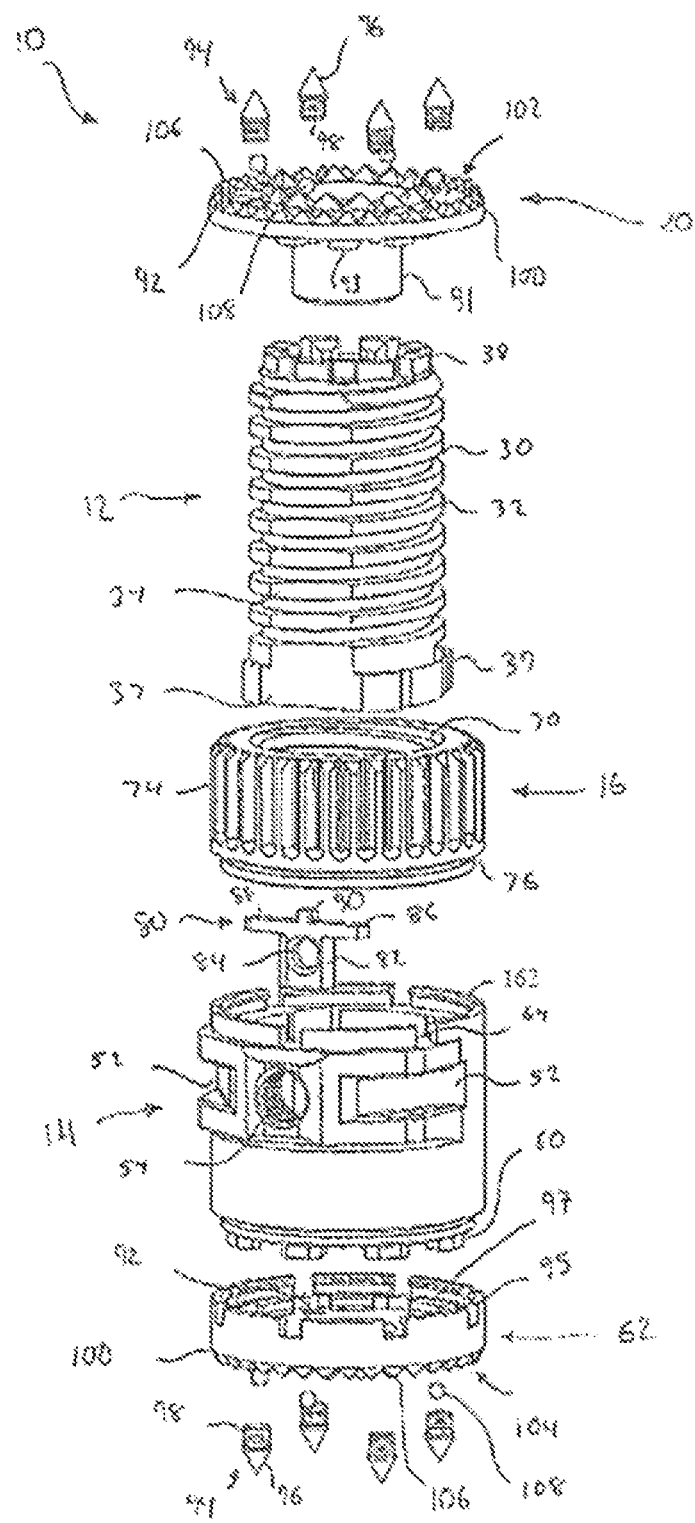
FIG. 2 is an exploded view of the implant of FIG. 1.
Figure 4:
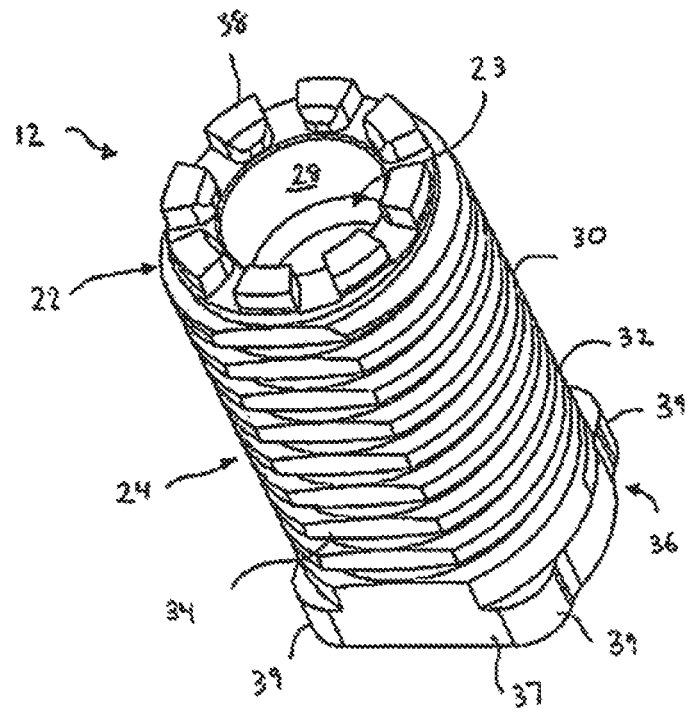
FIG. 4 is perspective view of an embodiment of an inner member of the implant of FIG. 1.

As seen in FIGS. 1-3, in a preferred embodiment, the teeth 74 are exposed to the exterior of prosthetic device 10. Because the teeth 74 are exposed around the periphery, little to no material is needed to cover up the exposed teeth, which generally makes the implant 10 lighter and easier to manufacture than prior art devices that require covering the gear teeth. In addition, the gear member 16 is more easily visible by a surgeon and more readily accessible by a rotation tool than devices that hide or cover gear teeth.

Referring to FIGS. 2, 5, and 7, in a preferred embodiment, the implant 10 also includes a locking member 80. The locking member 80 may be provided to substantially restrict all relative movement between inner member 12 and outer member 14, when, for example, the desired expansion of the prosthetic device 10 has been obtained. The locking member 80 has a body portion 82 with a through-hole 84. In a preferred embodiment, the body portion 82 has at least one, but preferably two, outwardly extending, flexible arms 86, 88 and at least one engagement member 90. In other preferred embodiments, instead of flexible arms 86, 88, it is contemplated that the locking member 80 may include an alternate biasing member, such as a leaf spring. The locking member 80 is configured and dimensioned to be received in the channel 57 of the outer member 14 in such a manner that the arms 86,88 rest against a shelf portion in the channel 57 and the through-hole 84 partially aligns with opening 54. The engagement member 90 preferably protrudes upwardly and is configured and dimensioned to engage the cutouts 73 of the gear member 16 to prevent the gear member 16 from rotating.

Referring now to FIGS. 1-3, in a preferred embodiment, the endplates 20, 62 are shown wherein the endplate 20 connects to the inner member 12 and endplate 62 connects to the outer member 14. In a preferred embodiment, endplate 20 includes an extension portion 91 which is received in the interior portion 23 of inner member 12, for example, in an interference or snap fit and includes a plurality of tabs 93 which interdigitate with tabs 38 to connect and position endplate 20 with respect to the inner member 12. Endplate 62 includes an extension portion 95 which engages the proximal end 44 of the outer member 14, for example, in an interference or snap fit and includes a plurality of tabs 97 which interdigitate with tabs 60 to connect and position endplate 62 with respect to the outer member 14. The endplates 20, 62 also preferably include hollow interior portions 99, 101 which are in fluid communication with the hollow interior portions 23, 50 of inner member 12 and outer member 14, respectively.

In a preferred embodiment, each endplate 20, 62 is generally annular in shape when viewed from the end or perpendicular to the longitudinal axis 18. It is, however, contemplated that the endplates 20, 62 can be other shapes including oblong, elliptical, kidney bean, polygonal, or geometric. Preferably, the endplates 20, 62 are designed to resemble or mimic the footprint of the vertebral body to which the endplates will engage. In this regard, endplates 20, 62 are configured to engage portions of the vertebrae in a predetermined orientation to maximize contact of the superior surface of the endplates 20, 62 with bone.

The dimensions of endplates 20, 62 can be varied to accommodate a patient's anatomy. In some embodiments, the endplates 20, 62 have a wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIGS. 1-3, in a preferred embodiment, the endplates 20, 40 include a plurality of mounting holes 92 spaced around the perimeter of each endplate 20, 40 for receiving insertable bone engaging members 94. In one embodiment, bone engaging members 94, comprise conical spikes 96 each having a cylindrical base portion 98 configured to fit within holes 92, for instance, by press-fit or by threaded engagement. In alternate embodiments, differently shaped bone engaging members 100 may be used, or in other embodiments no bone engaging members may be used. Referring again to FIG. 2, according to one embodiment, endplates 20, 62 have chamfered edges 100 around the perimeter to facilitate insertion and/or accommodate the shape of the vertebral bodies which they engage. The superior or bone engaging surfaces 102, 104 of endplates 20, 62 may also include numerous types of texturing to provide better initial stability and/or grasping contact between the end plate and the respective vertebrae. In a preferred embodiment, the texturing is a plurality of teeth 106. In preferred embodiments where the implant 10 is manufactured from PEEK or other plastic materials, the endplates 20, 62 may also include radio-opaque material, such as tantalum markers 108, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also endplates 20, 62 can be sized and shaped as well as positioned to accommodate different procedures and approached to the spine. For example, endplates 20, 62 may be made smaller for smaller statured patients or for smaller regions of the cervical spine. In addition, it is not required that endplates 20, 62 be shaped and sized identically and in alternate embodiments they can be shaped or sized differently than each other and/or include different bone engaging members or texturing.

Figure 8:
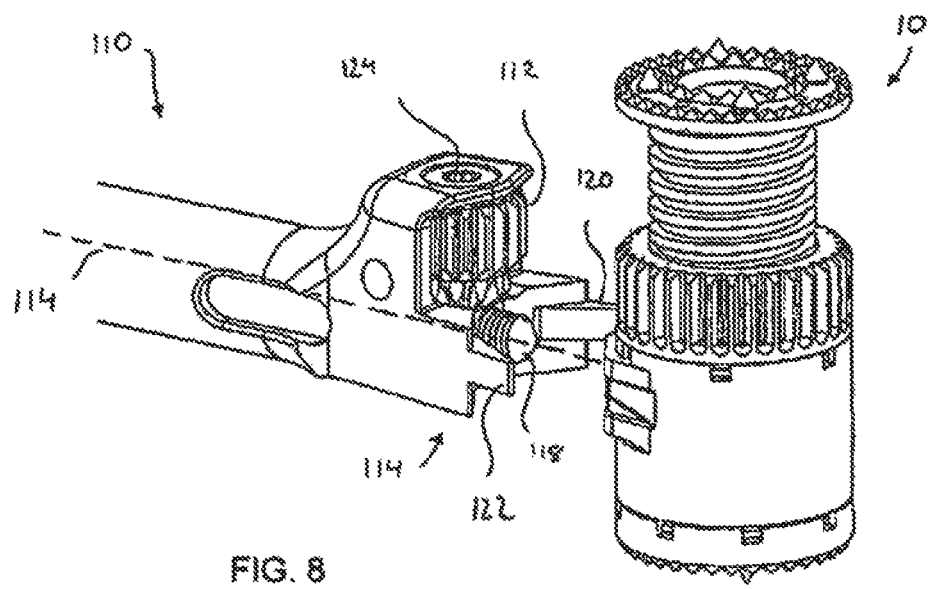
FIG. 8 is a perspective of one embodiment of a tool according to the present invention.
Figure 9:
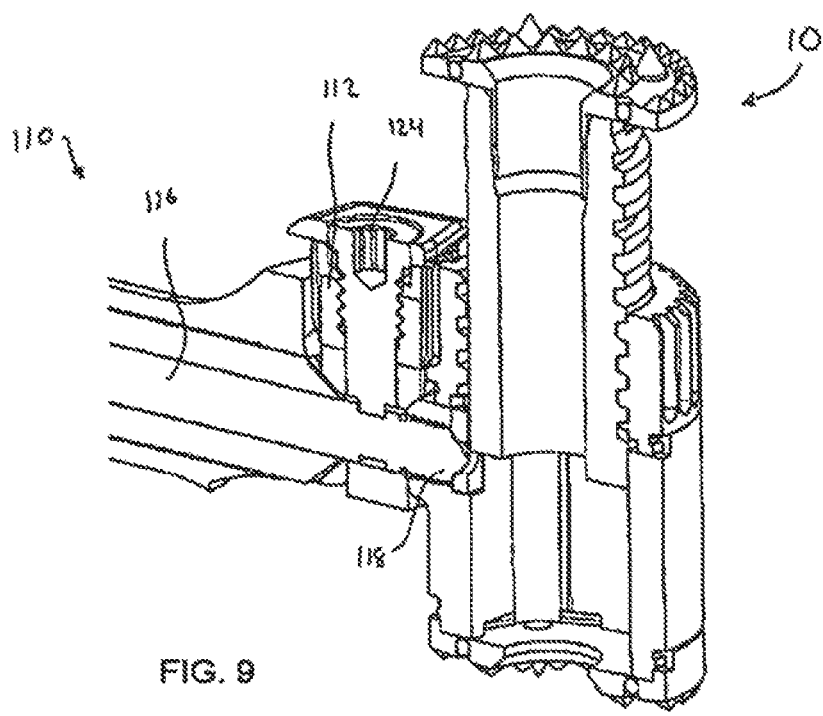
FIG. 9 is a cross-sectional view of the tool of FIG. 8 shown engaging an embodiment of an expandable implant according to the present invention.
Figure 10:
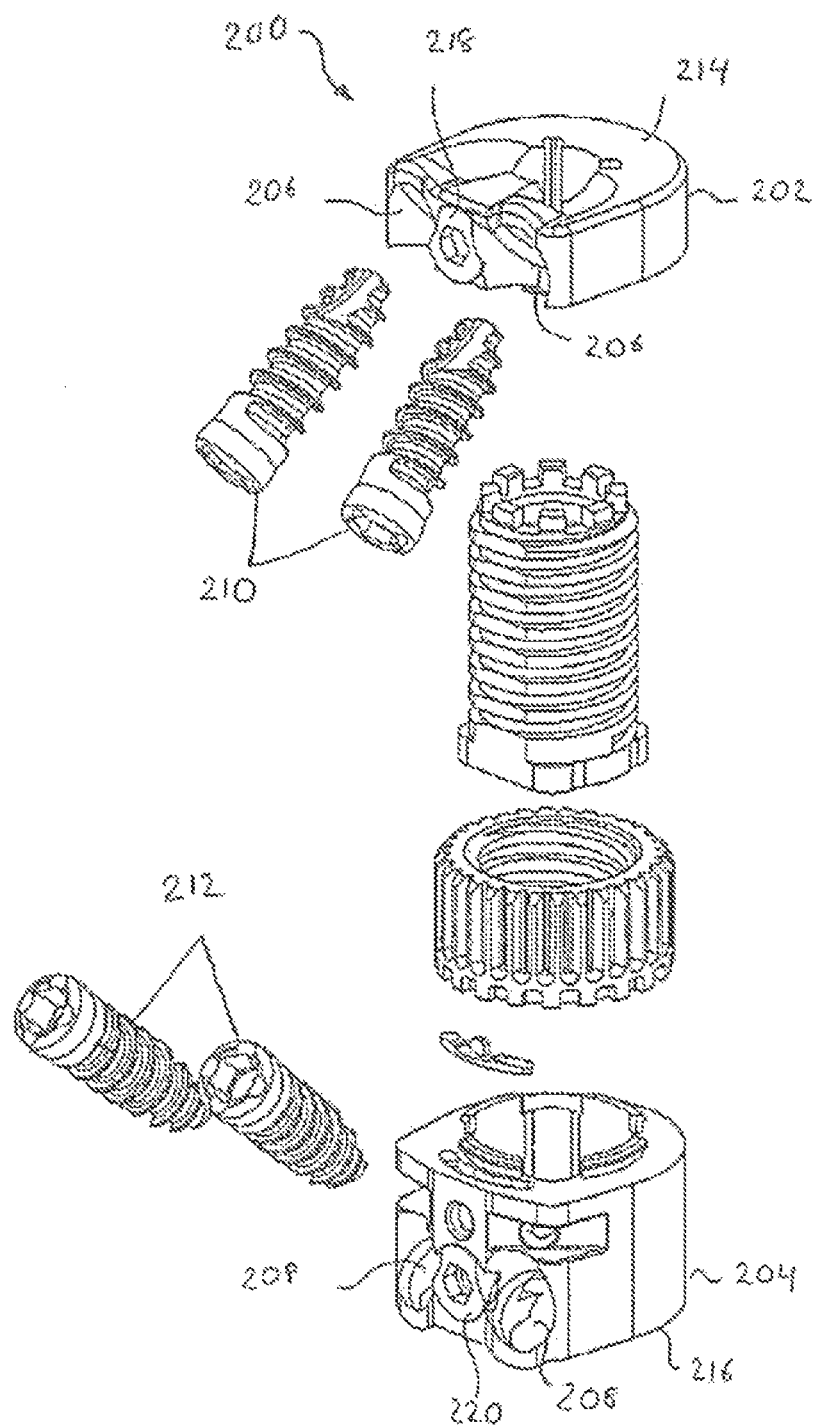
FIG. 10 is a perspective view of another embodiment of an implant according to the present invention.

Turning now to FIGS. 8-9, the implant 10 may be expanded by a tool 110 that includes a gear member 112 at its distal end 114. The tool 110 extends along a tool axis 114 and in operation the tool 110 is configured to engage the implant 10 such that the tool axis 114 is generally perpendicular to the longitudinal axis 18. The gear member 112 is configured to engage teeth 74 of the gear member 16 such that when the gear member 112 is rotated about the axis of the tool 110, the gear member 16 of the implant 10 is rotated about the longitudinal axis 18 and the inner member 12 translates along the longitudinal axis 18 to either expand or contract the implant 10. In a preferred embodiment, the tool 110 may include a central shaft 116 having a threaded distal tip portion 118 that extends distally beyond gear member 112 to facilitate location and mounting of tool 110 with the implant 10. The threaded distal tip portion 118 preferably includes a generally conical end portion and may be configured to extend radially through the opening 54 and threadably engage opening 54 in the outer member 14.

With continued reference to FIGS. 8-9, in one embodiment of prosthetic device 10 at least one, but preferably a plurality of mounting features or slots 52 are provided along the outer surface 48 of outer member 14. The tool 110 includes at least one, but preferably two, articulating arms 120, 122 that engage slots 52 for better engagement of the tool 110 with the implant 10 during insertion of the implant 10. In another preferred embodiment, the tool 110 may include arms 120, 122 that do not articulate.

In an exemplary use of the tool 110 with the implant 10, the tool 110 initially engages the slots 52 of the implant 10 via the arms 120, 122 and gear member 112 engages gear member 16 via their respective interdigitating teeth. A control member on the proximal end of the tool 110 (not shown) is manipulated to advance the central shaft 116 toward opening 54. The threaded tip portion 118 enters into opening 54 engaging the threads in opening 54 as well as engaging the through-hole 84 of locking member 80. It is also contemplated that the central shaft 116 is not movable with respect to the tool 110. In that embodiment, the entire tool 110 is moved so that the central shaft can enter and engage the opening 54 and the through-hole 84. As discussed earlier, the though-hole 84 is offset from opening 54, thus, when threaded tip 118 engages and advances into the opening 54 and the through-hole 84, the locking member 80 is pulled downwardly, riding along the conical edge of the tip 118 until the through-hole 84 is aligned with the opening 54. As the locking member 80 is pulled downwardly, the arms 82, 84 are flexed and the engagement member 90 disengages from the cutout 73 of the gear member 16 allowing the gear member 16 to rotate freely. The gear member 112 of tool 110 is then rotated via opening 114 which, in turn, rotates gear member 16. As discussed above, the rotation of gear member 16 results in the movement of inner member 12 causing the implant 10 to either expand or contract, depending on the direction the gear member 16 is rotated. Once the desired height for implant 10 is achieved, the tool member 110 is disengaged from implant 10. When the tool 110 is removed, the locking member 80 returns to the back to its initial position because of the arms 82, 84 returning back to their unflexed, at-rest state. The initial position of locking member 80 prevents the gear member 16 from turning because of the engagement of engagement member 90 with the cutouts 73. In that regard, implant 10 is locked from movement when the locking member 80 is in its initial position.

The benefit provided by the present locking mechanism is that it allows for a positive lock that engages and disengages automatically with the engagement and disengagement of the tool 110 with the implant 10, which minimizes the steps the surgeon must perform during the procedure.

Referring now to FIGS. 10-13, alternate preferred embodiments of endplates for the expandable implant 10 are shown. Looking at FIG. 10, in one variation, the endplates 202 and outer member 204 each include at least one screw hole 206, 208, but, preferably, each include two screw holes. The screw holes 206, 208 are configured and dimensioned to receive screws 210, 212. In a preferred embodiment, the screw holes 206, 208 are angled such that when the screws 210, 212 are seated in the screw holes 206, 208, the screws 210, 212 will extend outwardly from the superior surface 214 of endplate 202 and inferior surface 216 of outer member 204. Endplate 202 and outer member 204 also preferably include a locking element 218, 220 which, in a first position, allow the screws 210, 212 to back out from the seated position and, in a second position, block the screws 210, 212 from backing out of the seated position. In an exemplary use, once the implant 200 is installed and expanded to the desired position, the screws 210, 212 can be installed through the screw holes 206, 208 in such a manner as to purchase into the adjacent vertebral bodies. Once the screws 210, 212 are properly installed, including being engaged with the adjacent vertebral bodies, the locking elements 218, 220 can be actuated to block the screws 210, 212 from backing out of their installed position. The inclusion of screws 210, 212 in the endplate 202 and the outer member 204 provides for additional fixation of the implant 200 in the intervertebral space.

Figure 11:
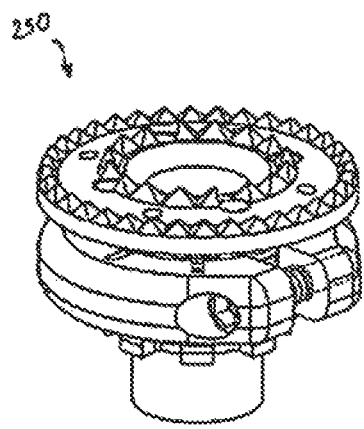
FIG. 11 is a perspective view of another embodiment of an endplate of an implant according to the present invention.
Figure 12:
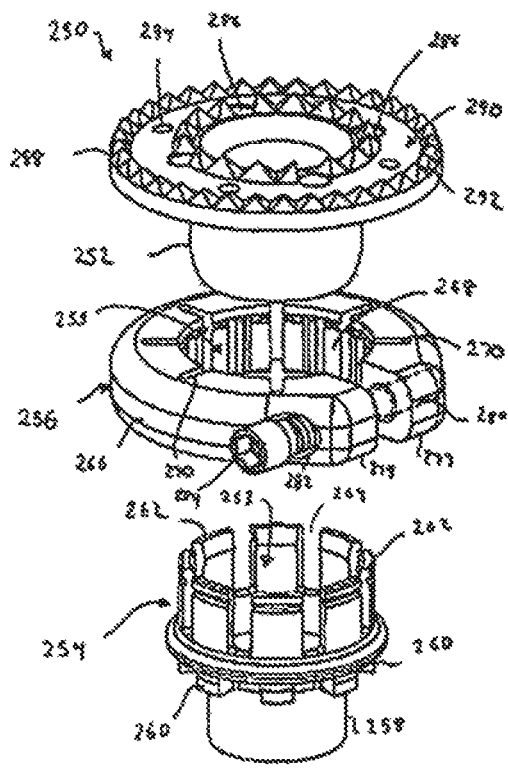
FIG. 12 is an exploded view of the endplate of FIG. 11.
Figure 13:
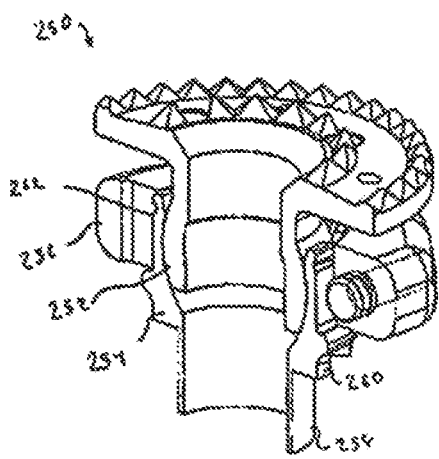
FIG. 13 is a cross-sectional view of the endplate of FIG. 11.

Turning to FIGS. 11-13, another preferred embodiment of an endplate 250 is shown. The endplate 250 is similar to endplate 20 but includes the additional functionality of being poly-axially rotatable with respect to an implant. In a preferred embodiment, endplate 250 includes a generally arcuate extension portion 252 which is received in an interior portion 253 of a receiving member 254 in such a manner as to allow the endplate 250 to move poly-axially with respect to the receiving member 254.

In a preferred embodiment, the receiving member 254 is received in an interior portion 255 of a locking ring 256. The receiving member 254 preferably includes a neck portion 258 as well as a plurality of tabs 260. The neck portion 258 is configured and dimensioned to be received within a hollow interior of an inner member, for example, in an interference or snap fit, and the plurality of tabs 260 interdigitate with tabs to connect and position the receiving member 254 with respect to an inner member. The receiving member 254 further includes a plurality of fingers 262 configured to cooperatively receive the extension portion 252 of endplate 250. A plurality of relief spaces or slots 264 are radially spaced between fingers 262 to allow fingers 262 to bend or flex radially.

In a preferred embodiment, the locking ring 256 has a generally annular, c-shape and includes an exterior wall 266, an interior wall 268, and ends 277, 279. The interior wall 268 preferably defines and interior portion 255. In a preferred embodiment, the interior wall 268 includes a plurality of channel 270 which are spaced radially along the locking ring 256. The channels 270 allow the locking ring 256 to bend or flex radially. The ends 277, 279 each include openings 280, 282 which may be partially threaded. A locking element 284 is configured and dimensioned to be threadingly received in the openings 280, 282. It also contemplated that that locking element 284 can engage the ends 277, 279 by other non-threaded means, such as a sliding fit.

With continued reference to FIGS. 11-13, in a preferred embodiment, the endplate 250 includes a plurality of mounting holes 286 spaced around the perimeter of the endplate 250 for receiving insertable bone engaging members. In one embodiment, bone engaging members, comprise conical spikes each having a cylindrical base portion configured to fit within holes 286, for instance, by press-fit or by threaded engagement. In alternate embodiments, differently shaped bone engaging members may be used, or in other embodiments no bone engaging members may be used. According to one preferred embodiment, endplate 250 has chamfered edges 288 around the perimeter to facilitate insertion and/or accommodate the shape of the vertebral bodies which they engage. The superior or bone engaging surfaces 290 of endplate 250 may also include numerous types of texturing to provide better initial stability and/or grasping contact between the end plate and the respective vertebrae. In a preferred embodiment, the texturing is a plurality of teeth 292. In preferred embodiments where the implant is manufactured from PEEK or other plastic materials, the endplate 250 may also include radio-opaque material, such as tantalum markers 294, which aid in providing location markers in radiographic images.

In an exemplary use, during the implant installation and expansion to the desired position, the endplate 250 can move in poly-axial fashion with respect to the implant to accommodate the anatomy of the adjacent vertebral body as well as accommodate the natural curvature of the spine, such as kyphosis and lordosis. More specifically, the arcuate extension portion 252 is free to move in the interior portion 253 of the receiving portion 254. The fingers 262 are generally compliant and can flex to accommodate the movement of the arcuate extension portion 252. Once the desired positioning of the endplate 250 is achieved, the endplate 250 can be locked in place. The endplate 250 is locked in place by actuating the locking element 284. As the element 284 engages the threading in opening 280,282 the ends 277, 279 of the locking ring 256 are brought closer together contracting the ring 254 and reducing the size of the interior portion 255. As the ring 254 contracts, the fingers 262 of the receiving member 254, abutting against the inner wall 268, are flexed radially inwardly pushing against the extension portion 252. As a result, the endplate 250 is locked in place.

Referring to FIGS. 14-19, another preferred embodiment of an expandable vertebral implant 300 is shown. The implant 300 preferably comprises an inner member 302 which may be telescopingly received within an outer member 304. The implant 300 further comprises a gear member 306 generally configured to effect translation of the inner member 302 with respect to the outer member 304 thereby allowing for expansion and contraction of the implant 300. The inner member 302, the outer member 304, and the gear member 306 are preferably centered along a longitudinal axis 308 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 302, 304, and 306 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 302, 304, and 306 may be made of a biologically inert metal alloys, such as titanium, or other suitable materials.

Referring to FIGS. 14-19, the inner member 302 has a generally cylindrical body 314 with a distal end 312 and a proximal end 326. In a preferred embodiment, the body 314 of the inner member 302 comprises an inner surface 318 and an outer surface 320 and generally defines a hollow interior portion 313 extending axially therethrough. At least part of the outer surface 320 preferably includes external threads 322. Located proximate to the distal end 312 of the body 314 are a plurality of tabs 328 which assist in connecting and positionally locating an endplate 310. In a preferred embodiment, the body 314 is configured and dimensioned to be cooperatively received within outer member 304.

Figure 15:
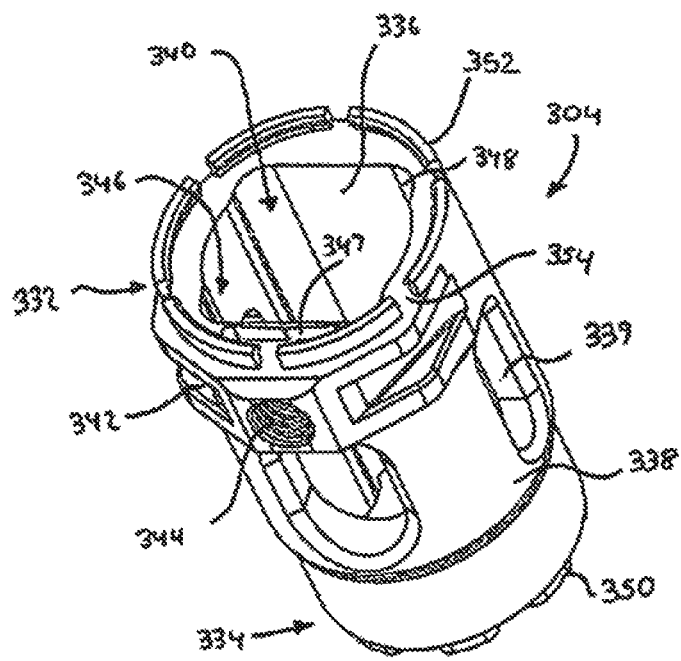
FIG. 15 is perspective view of an embodiment of an outer member of the implant of FIG. 14.

The outer member 304 has a generally cylindrical body 330 with a distal end 332 and a proximal end 334. In a preferred embodiment, the body 330 of the outer member 304 comprises an inner surface 336 and an outer surface 338 and generally defines a hollow interior portion 340 extending axially therethrough. In one preferred embodiment, extending from the outer surface 338 through the inner surface 336 is at least one opening 339 configured and dimensioned to allow access to the hollow interior portion 340. Opening 339 can be used as an access to pack the outer member 304 with bone growth material. The outer surface 338 preferably has at least one slot 342 and an opening 344 configured and dimensioned to receive a portion of an implantation tool. In a preferred embodiment, the opening 344 extends from the outer surface 338 to the hollow interior portion 340 and at least a portion of the opening 344 is threaded. As best seen in FIG. 15, the inner surface 336 includes a channel 347 for receiving a locking member (discussed below). Located proximate to the proximal end 334 of the outer member 304 are a plurality of tabs 350 which assist in connecting and positionally locating an endplate 352. In a preferred embodiment, a lip 352 is formed around the exterior of the distal end 332 of body 330 and is configured to cooperatively fit with a portion of the gear member 306. A plurality of relief spaces or slots 354 are radially spaced around lip 352 to facilitate a snapping engagement of the lip 352 with the gear member 306. In this regard, slots 354 allow the lip 352 to deform slightly and contract in the radial direction to accommodate gear member 306 to snap on to lip 352. In a preferred embodiment, the interior portion 340 of body 330 is configured and dimensioned to cooperatively receive body 314 of inner member 302 within outer member 304. In this regard, the dimensions of interior portion 340 of body 330 are greater than dimensions of body 314 of inner member 302.

Figure 14:
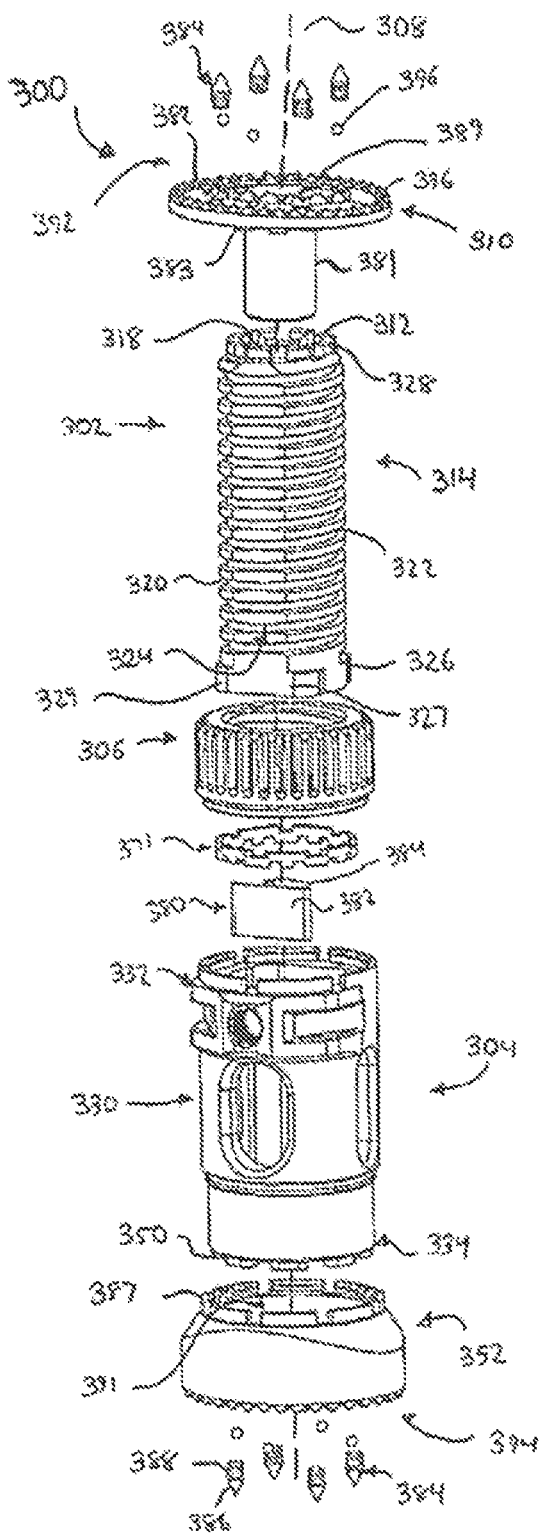
FIG. 14 is an exploded view of another embodiment of an implant according to the present invention.
Figure 19:
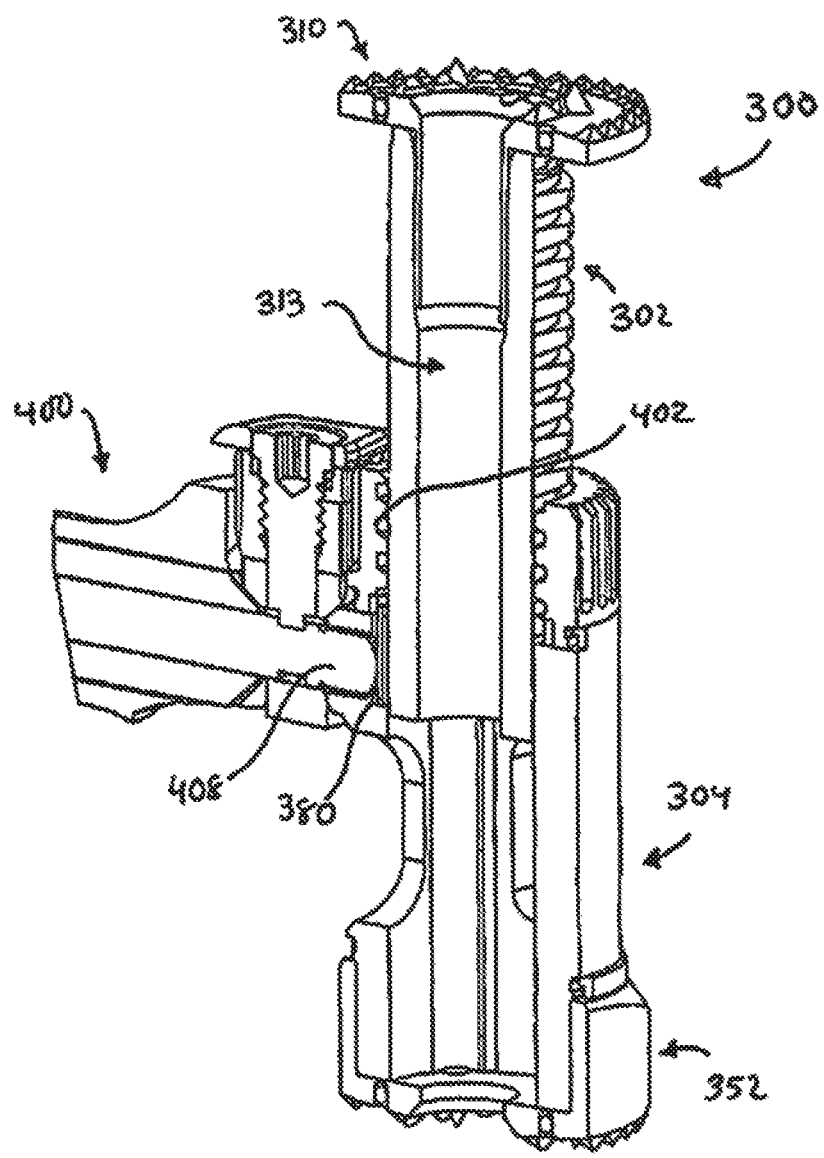
FIG. 19 is a cross-sectional view of the tool of FIG. 18 shown engaging an embodiment of an expandable implant according to the present invention.

As best seen in FIGS. 14, 15, and 19, in a preferred embodiment of a prosthetic device 300, the body 314 of the inner member 312 includes a flattened portion 324 which extends at least in part from the distal end 312 to the proximal end 326 and includes a base member 327 having at least one lobe 329 located proximate to the distal end 326 of the body 314. Focusing on FIG. 15, the body 330 of the outer member 304 includes a flattened area 346 and at least one depression 348 on the inner surface 336. When the inner member 302 is assembled within the outer member 304, the flattened area 346 of the outer member 304 cooperatively aligns with the flattened portion 324 of the inner member 302 and the at least one depression 348 of outer member 304 receives the at least one lobe 329 of the inner member 302. The flattened portion 324 and the flattened area 346 along with the lobes 329 and the depressions 348 cooperate to allow the inner member 302 to linearly move with respect to the outer member 304 but prevent the inner member 302 from rotating with respect to the outer member 304. In addition, the base member 327 serves as a stop preventing the inner member 302 from rotating to a point of disengagement from outer member 304.

Figure 16:
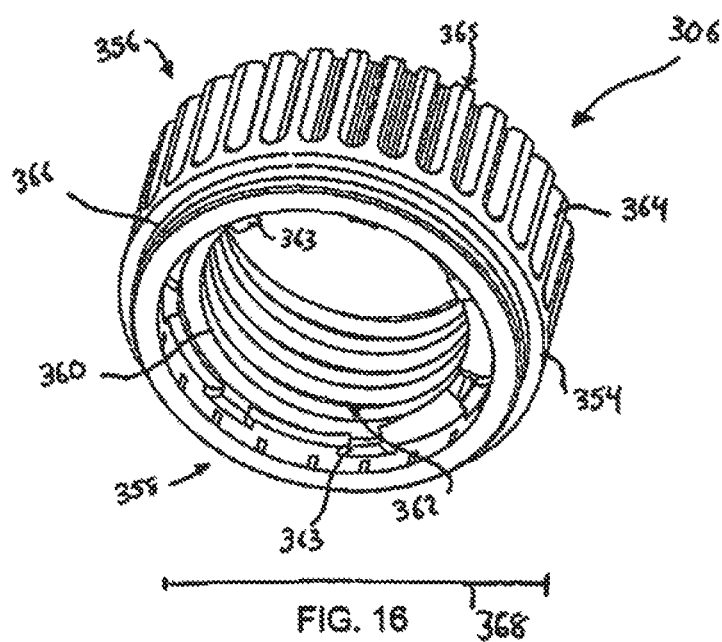
FIG. 16 is a perspective view of one embodiment of a gear member of the implant of FIG. 14.
Figure 17:
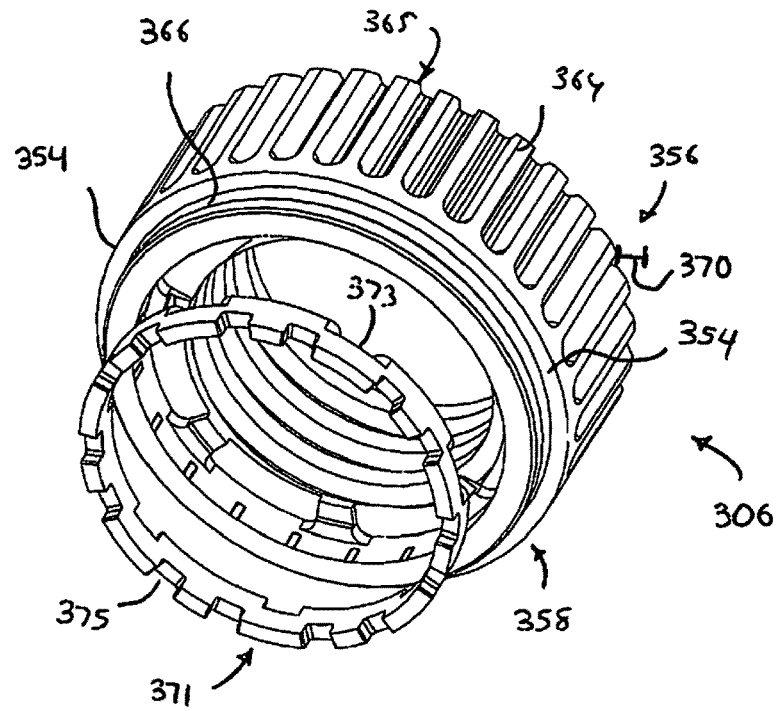
FIG. 17 is a perspective view of one embodiment of a gear member with an engagement element of the implant of FIG. 14.

Referring now to FIGS. 16-17, a gear member 306 comprises a generally hollow body 354 extending from a distal end 356 to a proximal end 358 with a helical thread 360 along at least part of an inner wall 362 and an array of gear teeth 364 along a portion of the exterior wall 365. The gear member 306 is generally configured to rotatably connect to the distal end 332 of the outer member 304 and the internal helical thread 360 is configured to engage the external threads 322 of the inner member 302 to cause translation of the inner member 302 with respect to the outer member 304. In a preferred embodiment, the gear member 306 includes a cylindrical cutout feature 366 extending around the inner wall 354 to cooperatively receive the lip 352 of the outer member 304. In this regard, the gear member 306 may rotate freely with respect to the outer member 304 while being retained from longitudinal and lateral movement. In a preferred embodiment, the gear member 306 also includes a series of engagement members 363 located proximate to the proximal end 358 for engaging a portion of a locking ring 371. In a preferred embodiment, the locking ring 371 is configured and dimensioned to be received in the gear member 306 and includes a plurality of slots 373 for engaging the engagement member 363 on a first end and includes a series of cutouts 375 for engaging a locking member on a second end. The engagement members 363 fit within the slots 373 in such a manner as to prevent the locking ring 371 from disengaging from the gear member 306. In one preferred embodiment, the locking ring 371 may be made of a different material than the gear member 306. For example, the locking ring may be made from titanium or other biocompatible metal and the gear member may be made from PEEK or other biocompatible polymer material.

With continued reference to FIGS. 16-17, the gear teeth 364 extend substantially from the proximal end 358 to the distal end 356 and extend around the entire periphery of at least a portion of the exterior wall 365. The outer-most external diameter 368 of the gear member 306 is sized to be the same as or slightly smaller than the smallest outer diameter of the endplates 310, 352 and the outer member 304. In this regard, when the implant 300 is viewed from the end in a plane perpendicular to the longitudinal axis 308, the gear member 306 does not protrude radially outward from beyond the perimeter of the endplates 310, 352.

As shown in FIG. 17, in a preferred embodiment, the gear teeth 364 extend a width 370 in a generally radial direction and generally extend radially outward to the outer diameter of the gear member 306. In this regard, the teeth 364 may be designed to have a width 370 to accommodate the expected gear forces given the particular gear ratio, types of material used, and desired overall diameter of prosthetic device 300. One skilled in the art will appreciate that the larger the outer diameter to which the teeth 364 radially extend, the larger the teeth 364 may be designed while still maintaining the same gear ratio. In this regard, when the teeth 364 are made larger, they generally have a better mechanical strength. Also, the ability to design larger, wider, and stronger teeth 364 is advantageous for embodiments where the implant 300 is made of PEEK, other plastic, or other non-metallic materials that may have less mechanical strength than, for instance, titanium.

Furthermore, as described in one embodiment, because the outer-most diameter of the gear member 306 may be as large as the outer diameter of the endplates 310, 352, and the teeth 364 extend radially to the outer-most diameter of the gear member 306, a larger inner diameter of the gear member 306 may be manufactured without compromising mechanical gear strength. As a result, a larger overall inner diameter of the implant 300 may be accommodated which allows the packing of more bone material therein and facilitates bone fusion once the implant 300 is implanted.

As seen in FIG. 14, in a preferred embodiment, the teeth 364 are exposed to the exterior of prosthetic device 300. Because the teeth 364 are exposed around the periphery, little to no material is needed to cover up the exposed teeth, which generally makes the implant 300 lighter and easier to manufacture than prior art devices that require covering the gear teeth. In addition, the gear member 306 is more easily visible by a surgeon and more readily accessible by a rotation tool than devices that hide or cover gear teeth.

Figure 18:
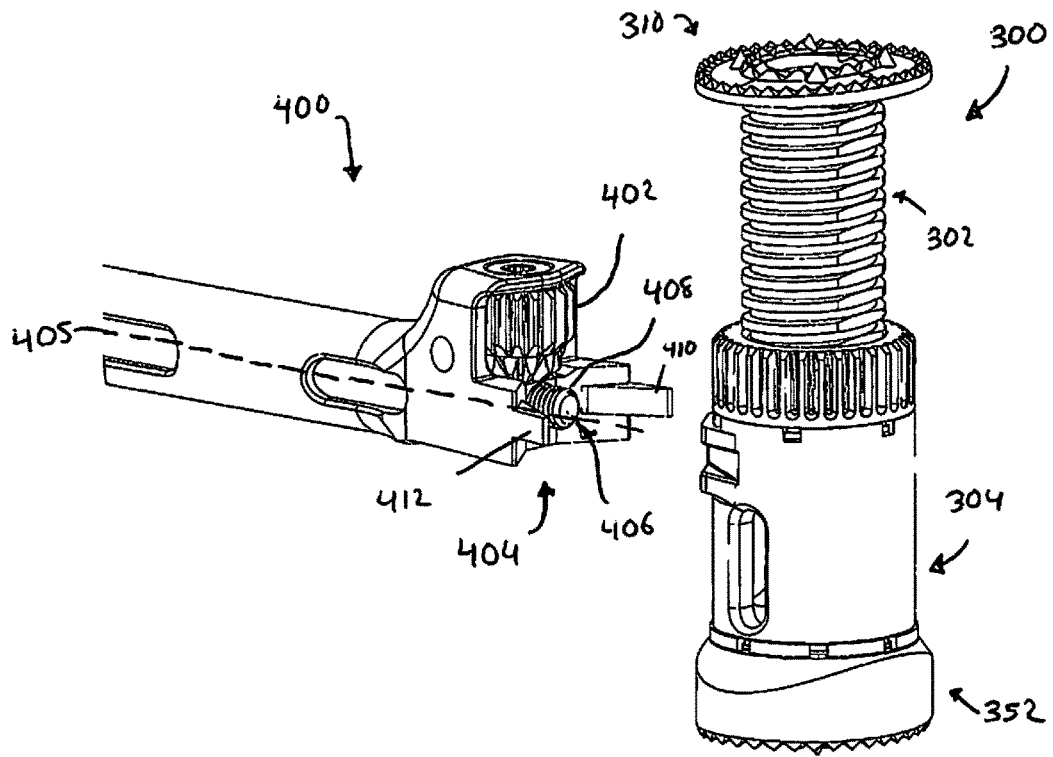
FIG. 18 is a perspective of one embodiment of a tool according to the present invention.

Referring to FIGS. 14, 18, and 19, in a preferred embodiment, the implant 300 also includes a locking member 380. The locking member 380 may be provided to substantially restrict all relative movement between inner member 302 and outer member 304, when, for example, the desired expansion of the prosthetic device 300 has been obtained. The locking member 380 has a body portion 382 with an engagement member 384. In a preferred embodiment, the body portion 382 is dimensioned to be flexible allowing the locking member 380 to flex but return to its original configuration or orientation. The locking member 380 is configured and dimensioned to be received in the channel 347 of the outer member 304 in such a manner that body portion 382 aligns with opening 344. The engagement member 384 preferably protrudes upwardly and is configured and dimensioned to engage the cutouts 375 of the locking ring 371, which is fixed to the gear member 306, to prevent the gear member 306 from rotating.

Referring now to FIG. 14, in a preferred embodiment, the endplates 310, 352 are shown wherein the endplate 310 connects to the inner member 302 and endplate 352 connects to the outer member 304. In a preferred embodiment, endplate 310 includes an extension portion 381 which is received in the interior portion 313 of inner member 302, for example, in an interference or snap fit and includes a plurality of tabs 383 which interdigitate with tabs 328 to connect and position endplate 310 with respect to the inner member 302. Endplate 352 includes a plurality of tabs 387 which interdigitate with tabs 350 to connect and position endplate 352 with respect to the outer member 304. The endplates 310, 352 also preferably include hollow interior portions 389, 391 which are in fluid communication with the hollow interior portions 313, 340 of inner member 302 and outer member 304, respectively.

In a preferred embodiment, each endplate 310, 352 is generally annular in shape when viewed from the end or perpendicular to the longitudinal axis 308. It is, however, contemplated that the endplates 310, 352 can be other shapes including oblong, elliptical, kidney bean, polygonal, or geometric. Preferably, the endplates 310, 352 are designed to resemble or mimic the footprint of the vertebral body to which the endplates will engage. In this regard, endplates 310, 352 are configured to engage portions of the vertebrae in a predetermined orientation to maximize contact of the superior surface of the endplates 310, 352 with bone.

The dimensions of endplates 310, 352 can be varied to accommodate a patient's anatomy. In some embodiments, the endplates 310, 352 have a wedge-shaped profile to accommodate the natural curvature of the spine. In anatomical terms, the natural curvature of the lumbar spine is referred to as lordosis. When implant 300 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIG. 14, in a preferred embodiment, the endplates 310, 330 include a plurality of mounting holes 382 spaced around the perimeter of each endplate 310, 330 for receiving insertable bone engaging members 384. In one embodiment, bone engaging members 384, comprise conical spikes 386 each having a cylindrical base portion 388 configured to fit within holes 382, for instance, by press-fit or by threaded engagement. In alternate embodiments, differently shaped bone engaging members 384 may be used, or in other embodiments no bone engaging members may be used. Referring again to FIG. 14, according to one embodiment, endplates 310, 352 have chamfered edges around the perimeter to facilitate insertion and/or accommodate the shape of the vertebral bodies which they engage. The superior or bone engaging surfaces 392, 394 of endplates 310, 352 may also include numerous types of texturing to provide better initial stability and/or grasping contact between the end plate and the respective vertebrae. In a preferred embodiment, the texturing is a plurality of teeth 396. In preferred embodiments where the implant 10 is manufactured from PEEK or other plastic materials, the endplates 310, 352 may also include radio-opaque material, such as tantalum markers 398, which aid in providing location markers in radiographic images.

In preferred embodiments, the length, diameter, and shape of prosthetic device 300 may vary to accommodate different applications, different procedures, implantation into different regions of the spine, or size of vertebral body or bodies being replaced or repaired. For example, implant 300 may be expandable to a longer distance to replace multiple vertebral bodies. Also endplates 310, 352 can be sized and shaped as well as positioned to accommodate different procedures and approached to the spine. For example, endplates 310, 352 may be made smaller for smaller statured patients or for smaller regions of the cervical spine. In addition, it is not required that endplates 310, 352 be shaped and sized identically and in alternate embodiments they can be shaped or sized differently than each other and/or include different bone engaging members or texturing.

Turning now to FIGS. 18-19, the implant 300 may be expanded by a tool 400 that includes a gear member 402 at its distal end 404. The tool 400 extends along a tool axis 405 and in operation the tool 400 is configured to engage the implant 300 such that the tool axis 405 is generally perpendicular to the longitudinal axis 308. The gear member 402 is configured to engage teeth 364 of the gear member 306 such that when the gear member 402 is rotated, the gear member 402 of the implant 400 is rotated about the longitudinal axis 18 and the inner member 302 translates along the longitudinal axis 308 to either expand or contract the implant 300. In a preferred embodiment, the tool 400 may include a central shaft 406 having a threaded distal tip portion 408 that extends distally beyond gear member 402 to facilitate location and mounting of tool 400 with the implant 300. The threaded distal tip portion 408 preferably includes a generally conical end portion and may be configured to extend radially through the opening 344 and threadably engage opening 344 in the outer member 304.

With continued reference to FIGS. 18-19, in one embodiment of prosthetic device 300 at least one, but preferably a plurality of mounting features or slots 342 are provided along the outer surface 338 of outer member 304. The tool 400 includes at least one, but preferably two, arms 410, 412 that engage slots 342 for better engagement of the tool 400 with the implant 300 during insertion of the implant 300. In another preferred embodiment, the tool 400 may include arms 410, 412 that articulate.

In an exemplary use of the tool 400 with the implant 300, the tool 400 initially engages the slots 342 of the implant 300 via the arms 410, 412 and gear member 402 engages gear member 306 via their respective interdigitating teeth. A control member on the proximal end of the tool 400 (not shown) is manipulated to advance the central shaft 406 toward opening 344. The threaded tip portion 408 enters into opening 344 engaging the threads in opening 344 as well as engaging the body 382 of locking member 380. It is also contemplated that the central shaft 406 is not movable with respect to the tool 400. In that embodiment, the entire tool 400 is moved so that the central shaft can enter and engage the opening 344 and the body 382. When threaded tip portion 408 engages and advances into the opening 344 and pushes against body 382 of the locking member 380, the locking member 380 is flexed inwardly toward the center of the implant 300. As the locking member 380 flexes inwardly, the engagement member 384 disengages from the cutout 375 of the locking ring 371, which is fixed to the gear member 306, allowing the gear member 306 to rotate freely. The gear member 402 of tool 400 is then rotated which, in turn, rotates gear member 306. As discussed above, the rotation of gear member 306 results in the movement of inner member 302 causing the implant 300 to either expand or contract, depending on the direction the gear member 306 is rotated. Once the desired height for implant 300 is achieved, the tool member 400 is disengaged from implant 300. When the tool 400 is removed, the locking member 380 returns to the back to its initial position because the threaded tip portion 408 is no longer pushing against the body 382 of the locking member 380 causing it to flex inwardly. The initial position of locking member 380 prevents the gear member 306 from turning because of the engagement of engagement member 384 with the cutouts 375 of the locking ring 371. In that regard, implant 300 is locked from movement when the locking member 380 is in its initial position.

The benefit provided by the present locking mechanism is that it allows for a positive lock that engages and disengages automatically with the engagement and disengagement of the tool 400 with the implant 300, which minimizes the steps the surgeon must perform during the procedure.

Figure 20:
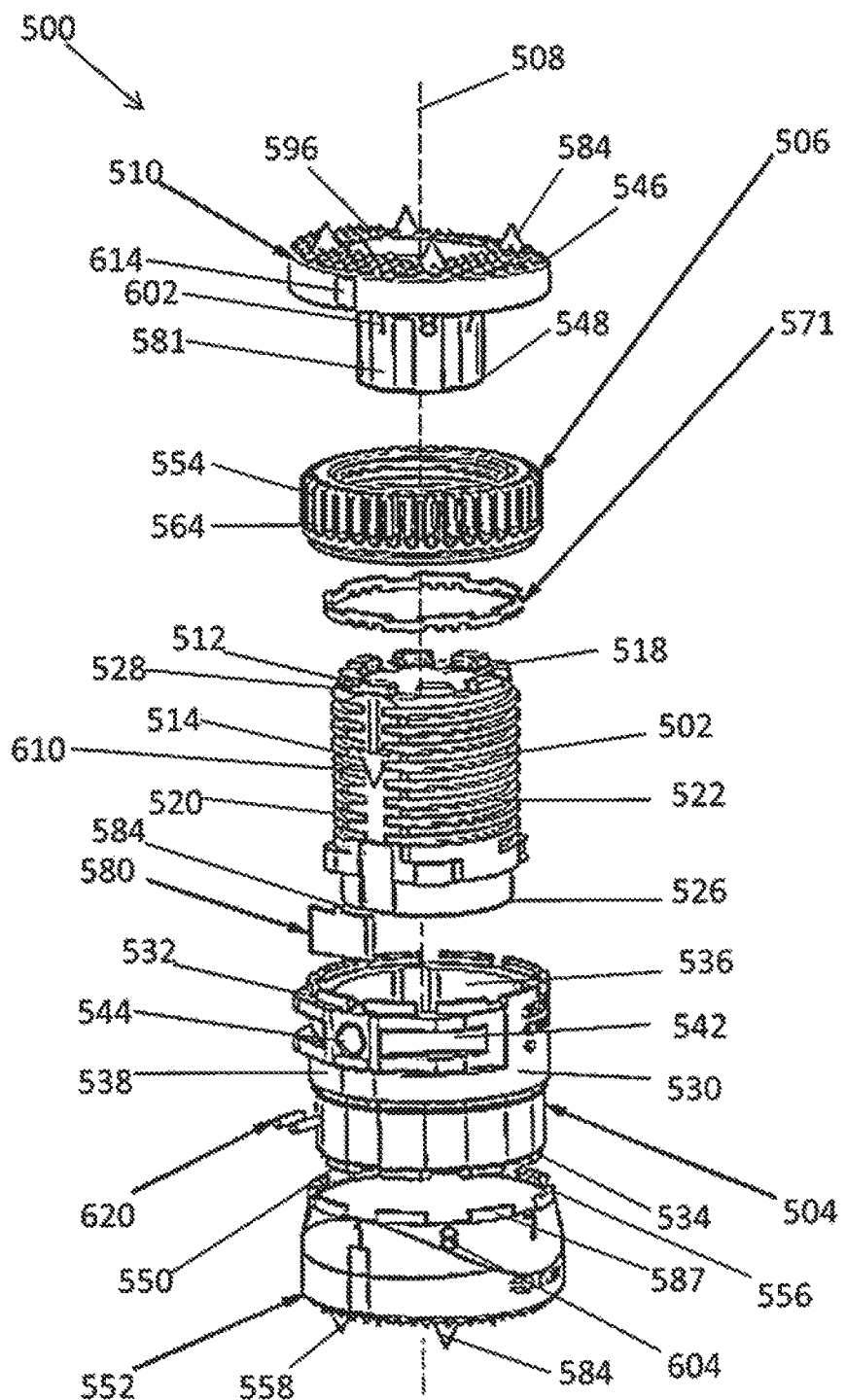
FIG. 20 is an exploded view of an implant according to another embodiment.

Referring to FIGS. 20-22, another preferred embodiment of an expandable vertebral implant 500 is shown. Implant 500 is similar to implant 300 discussed above. The implant 500 includes an inner member 502 which may be telescopingly received within an outer member 504. The implant 500 further comprises a gear member 506 generally configured to effect translation of the inner member 502 with respect to the outer member 504 thereby allowing for expansion and contraction of the implant 500. The inner member 502, the outer member 504, and the gear member 506 are preferably centered along a longitudinal axis 508 and define a hollow interior portion which may be filled with bone material, bone growth factors, bone morphogenic proteins, or other materials for encouraging bone growth, blood vessel growth or growth of other tissue through the many apertures in the device. In addition, the implant 500 may include one or more endplates 510, 552 configured to engage adjacent vertebrae.

Referring to FIG. 20, the inner member 502 has a generally cylindrical body 514 with a distal end 512 and a proximal end 526. In a preferred embodiment, the body 514 of the inner member 502 comprises an inner surface 518 and an outer surface 520 and generally defines a hollow interior portion extending axially therethrough. At least part of the outer surface 520 preferably includes external threads 522. Located proximate to the distal end 512 of the body 514 are a plurality of tabs 528 which assist in connecting and positionally locating the endplate 510. In a preferred embodiment, the body 514 of the inner member 502 is configured and dimensioned to be cooperatively received within outer member 504.

The outer member 504 has a generally cylindrical body 530 with a distal end 532 and a proximal end 534. In a preferred embodiment, the body 530 of the outer member 504 comprises an inner surface 536 and an outer surface 538 and generally defines a hollow interior portion extending axially therethrough. The outer surface 538 may include at least one slot 542 and an opening 544 configured and dimensioned to receive a portion of an implantation tool. In a preferred embodiment, the opening 544 extends from the outer surface 538 to the hollow interior portion and at least a portion of the opening 544 is threaded. The inner surface 536 includes a channel for receiving a locking member 580. Located proximate to the proximal end 534 of the outer member 504 are a plurality of tabs 550 which assist in connecting and positionally locating the endplate 552. For example, a lip may be formed around the exterior of the distal end 532 of body 530 and is configured to cooperatively fit with a portion of the gear member 506. A plurality of relief spaces or slots may be radially spaced around the lip to facilitate a snapping engagement of the lip with the gear member 506. The interior portion of the outer member 504 may be configured and dimensioned to cooperatively receive the inner member 502.

Figures 22A, 22B:
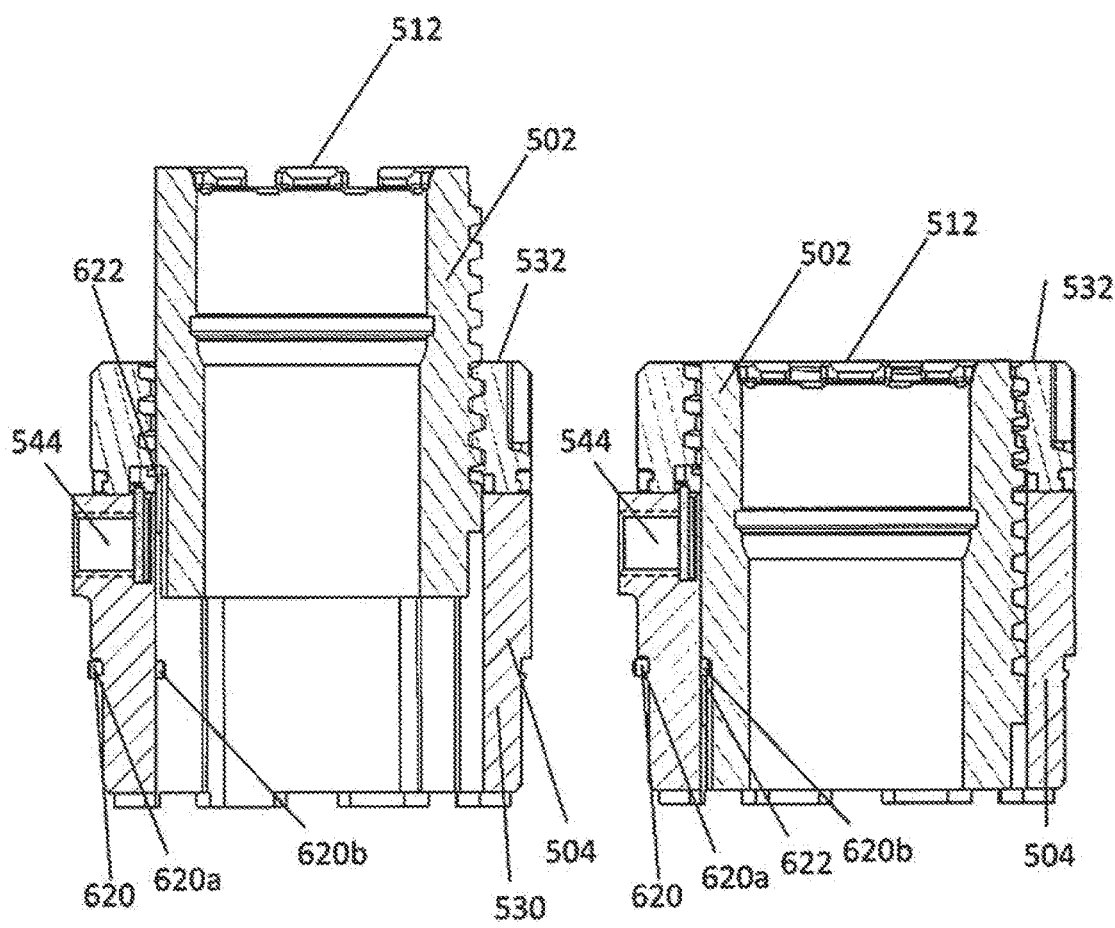
FIGS. 22a and 22b are close-up cross-sectional views of the inner and outer members shown in FIG. 20.

As shown in FIG. 22*a*, the inner member 502 may include at least one longitudinal groove 622 or a series of grooves extending along a length of the inner member 502. In particular, the longitudinal groove 622 may extend along a portion of the outer surface 520 or the external portion of the inner member 502. The groove 622 may be a cutout extending a depth into the inner member 502 or may extend through the entire wall of the inner member 502. The longitudinal groove 622 may be positioned substantially parallel to the longitudinal axis 508 of the implant 500. The longitudinal groove 622 is configured to engage a pin 620 protruding from the outer member 504 such that the pin 620, when engaged in the groove 622, prevents the inner member 502 from translating completely through the outer member 504. In other words, the pin 620 aids in the implant functionality by preventing the inner member 502 from recessing too deeply into the outer member 504 or from disassembling from the outer member 504. In addition, the pin 620 is configured to aid in alignment and limit rotation of the second endplate 552.

Referring to FIGS. 22*a* and 22*b*, the pin 620 may include a first end 620*a* and a second end 620*b*. The pin 620 may extend through a wall of the outer member 504 such that the second end 620*b* is configured to engage the groove 622 in the inner member 502. The pin 620 may protrude from an outer surface and/or an inner surface of the outer member 504. The pin 620 may be configured to fit in one of the gaps between a plurality tabs 587 on the distal end 556 of the second endplate 552 to aid in alignment and limit rotation of the second endplate 552. As shown in FIG. 22*b*, the pin 620 may engage with an uppermost surface of the groove 622 to prevent the inner member 504 from translating through an opening in a proximal end 534 of the outer member 504 (e.g., from translating completely through the outer member 504).

The pin 620 may be fixed, pressed, fitted, or machined into the outer member 504. The pin 620 may be a separate piece or may be integral with the outer member 504. The pin 620 may be positioned transversely to the outer member 504 (e.g., perpendicular to the longitudinal axis 508). Although the pin 620 is depicted as cylindrical in shape, the pin 620 may have any suitable shape and form, such as square, rectangular, conical, pyramidal, oblong, polygonal, or other suitable shape or cross-section to engage the groove 622. In addition, the pin 620 may have an elongate body, which is solid or hollow therethrough.

Figure 21A:
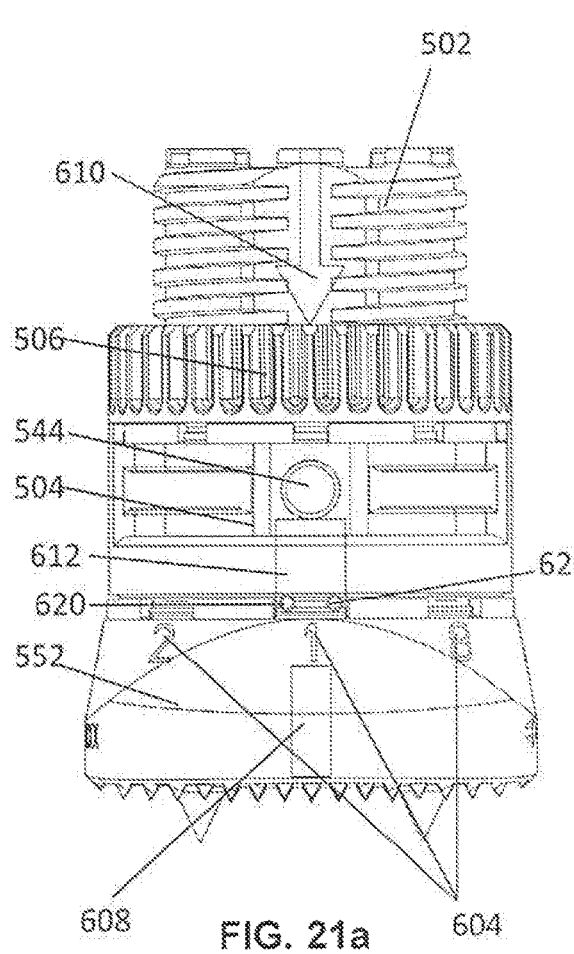
FIGS. 21a and 21b are close-up side views of the embodiment shown in FIG. 20.

The inner member 502 may include additional grooves 622 including a second longitudinal groove (not shown) positioned substantially parallel to the first groove 622 and configured to receive a second pin 620 protruding from the outer member 504. For example, FIG. 21*a* depicts two pins 620 positioned proximate to the proximal end 534 of the outer member 504, located parallel to one another, and centered along the longitudinal axis 508 of the implant 500. The pins 620 can function in two different ways: (1) the pins 620 can aid in alignment of the lower endplate 552 during its assembly to the outer member 504 by fitting between the tabs 587 on the lower endplate 552; and (2) the pins 620 serve to prevent downward translation of the inner member 502 within the outer member 504 past a specific point, including preventing disassembly of the implant 500.

The gear member 506 comprises a generally hollow body 554 extending from a distal end to a proximal end with a helical thread along at least part of an inner wall and an array of gear teeth 564 along a portion of its exterior wall. The gear member 506 is generally configured to rotatably connect to the distal end 532 of the outer member 504 and the internal helical thread is configured to engage the external threads 522 of the inner member 502 to cause translation of the inner member 502 with respect to the outer member 504. The gear member 506 may include a cylindrical cutout feature extending around the inner wall to cooperatively receive the lip of the outer member 504. In this regard, the gear member 506 may rotate freely with respect to the outer member 504 while being retained from longitudinal and lateral movement. In a preferred embodiment, the gear member 506 also includes a series of engagement members located proximate to the proximal end for engaging a portion of a locking ring 571. In a preferred embodiment, the locking ring 571 is configured and dimensioned to be received in the gear member 506 and includes a plurality of slots for engaging the engagement member on a first end and includes a series of cutouts for engaging a locking member 580 on a second end.

The implant 500 may also include a locking member 580. The locking member 580 may be provided to substantially restrict all relative movement between inner member 502 and outer member 504, when, for example, the desired expansion of the prosthetic device 500 has been obtained. The locking member 580 has a body portion with an engagement member 584. In a preferred embodiment, the body portion is dimensioned to be flexible allowing the locking member 580 to flex but return to its original configuration or orientation. The locking member 580 is configured and dimensioned to be received in the channel of the outer member 504 in such a manner that body portion aligns with opening 544. The engagement member 584 preferably protrudes upwardly and is configured and dimensioned to engage the cutouts of the locking ring 571, which is fixed to the gear member 506, to prevent the gear member 506 from rotating.

The endplates 510, 552 are configured to engage portions of the vertebrae in a predetermined orientation to maximize contact of the superior surface of the endplates 510, 552 with bone. The upper endplate 510 includes a distal end 546 configured to engage the superior vertebra and a proximal end 548 configured to engage the inner member 502. The lower endplate 552 includes a distal end 556 configured to engage the outer member 504 and a proximal end 558 configured to engage the inferior vertebra. When assembled, endplate 510 connects to the inner member 502 and endplate 552 connects to the outer member 504. The endplates 510, 552 may be axially applied onto the inner and outer members 502, 504, respectively, when assembled. In a preferred embodiment, endplate 510 includes an extension portion 581 which is at least partially received in the interior portion of inner member 502. In particular, the extension portion 581 may include a proximal portion of the endplate 510 including proximal end 548. The extension portion 581 may be recessed compared to the portion of the endplate 510 which contacts the vertebra. The extension portion 581 may be generally cylindrical in shape. The extension portion 581 may be received in the inner member 502, for example, in an interference or snap fit. The distal end 556 of endplate 552 may include a plurality of tabs 587 which interdigitate with tabs 550 to connect and position endplate 552 with respect to the outer member 504. The endplates 510, 552 also preferably include hollow interior portions which are in fluid communication with the hollow interior portions of the inner and outer members 502, 504, respectively.

The endplates 510, 552 may be provided with bone engaging members 584. For example, the bone engaging members 584 may comprise conical spikes. In alternate embodiments, differently shaped bone engaging members 584 may be used, or in other embodiments no bone engaging members may be used. The endplates 510, 552 may have chamfered edges around the perimeter to facilitate insertion and/or accommodate the shape of the vertebral bodies which they engage. The bone engaging surfaces of the endplates 510, 552 may also include numerous types of texturing to provide better initial stability and/or grasping contact between the end plate and the respective vertebrae. In a preferred embodiment, the texturing includes a plurality of teeth 596.

Depending on the orientation and positioning of the implant 500, the endplates 510, 552 may be provided with a certain degree of lordosis or kyphosis to mimic a natural or unnatural curvature of the spine. In order to facilitate the proper alignment of the implant 500, endplate 510 may be provided with a first series of markings 602 and endplate 552 may be provided with a corresponding second series of markings 604. When at least one of the first and second sequential numbers one through eight are positioned around the perimeter of endplate 510.

Similarly, the second series of markings 604 preferably includes a plurality of different markings which correspond to the first series of markings 602. Accordingly, eight different numeric markings including sequential numbers one through eight, which match the sequential numbers provided on endplate 510, are positioned around the perimeter of endplate 552. These markings 602, 604 may be visually aligned with one another with or without additional markers on the implant 500. In this way, when one of the first series of markings 602 is aligned with the one of the second series of markings 604, the endplates 510, 552 are positioned and aligned for a given implantation approach. As shown in the embodiment shown in FIG. 20, the number "1" on endplate 510 is aligned with the number "1" on endplate 552. Although depicted as numeric characters, the first and second series of markings 602, 604 may be any suitable markings, characters, indicia, or the like that can be visually identified and aligned to match the first and second endplates 510, 552. Table 1 depicts a sample key to identify types of alignment for the first and second markings 602, 604 for a user.

TABLE 1

| Key | | | | | |
|---|---|---|---|---|---|
| Implant Upright | | | Implant Upside-Down | | |
| Approach | Lordosis | Key | Approach | Lordosis | Key |
| Anterior | Lordosis | 1 | Anterior | Lordosis | 1 |
| Anterolateral Right | Lordosis | 2 | Anterolateral Left | Lordosis | 2 |
| Direct Lateral Right | Lordosis | 3 | Direct Lateral Left | Lordosis | 3 |
| Posterolateral Right | Lordosis | 4 | Posterolateral Left | Lordosis | 4 |
| Posterolateral Left | Lordosis | 6 | Posterolateral Right | Lordosis | 6 |
| Direct Lateral Left | Lordosis | 7 | Direct Lateral Right | Lordosis | 7 |
| Anterolateral Left | Lordosis | 8 | Anterolateral Right | Lordosis | 8 |
| Implant Upright | | | Implant Upside-Down | | |
| Approach | Kyphosis | Key | Approach | Kyphosis | Key |
| Posterolateral Left | Kyphosis | 2 | Posterolateral Right | Kyphosis | 2 |
| Direct Lateral Left | Kyphosis | 3 | Direct Lateral Right | Kyphosis | 3 |
| Anterolateral Left | Kyphosis | 4 | Anterolateral Right | Kyphosis | 4 |
| Anterior | Kyphosis | 5 | Anterior | Kyphosis | 5 |
| Anterolateral Right | Kyphosis | 6 | Anterolateral Left | Kyphosis | 6 |
| Direct Lateral Right | Kyphosis | 7 | Direct Lateral Left | Kyphosis | 7 |
| Posterolateral Right | Kyphosis | 8 | Posterolateral Right | Kyphosis | 8 | series of markings 602, 604 are aligned, the first and second endplates 510, 552 are aligned for a specific approach to the spine (e.g., anterior implantation) and to provide the desired lordosis or kyphosis. The marking scheme (e.g., numbering scheme) aids in assembly of the endplates 510, 552 to the other components of the implant (e.g., the inner and outer members 502, 504) by allowing a user to align the markings for varying approaches to the spine.

The first and second series of markings 602, 604 may include characters, alphanumeric characters, numeric characters, colors, symbols, shapes, words, pictures, or similar indicia. These markings 602, 604 may be etched, engraved, or otherwise marked or applied on the endplates 510, 552. The first series of markings 602 preferably includes a plurality of different markings. In other words, the first series of markings 602 preferably includes a plurality of markings that do not repeat and are not the same. As partially shown in FIG. 20, eight different numeric markings including The first and second series of markings 602, 604 may be positioned at any suitable location on the implant 500. The first series of markings 602 may be positioned at intervals around a perimeter of endplate 510. In particular, the first series of markings 602 may be positioned around a perimeter of the extension portion 581 of the endplate 510. The first series of markings 602 may be offset a distance from the proximal end 548 of the endplate 510. The second series of markings 604 may be positioned at intervals, identical to the first series of markings 602, around a perimeter of endplate 552. In particular, the second series of markings 604 may be positioned proximate to the distal end 556 and the plurality of tabs 587 that connect endplate 552 to the outer member 504.

Figure 21B:
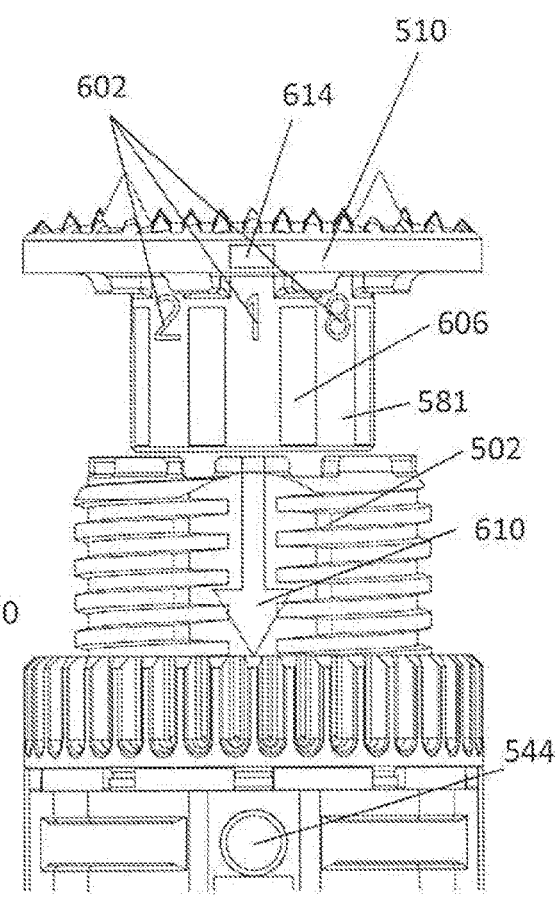

In order to aid in alignment between the first and second series of markings 602, 604 additional markings may be provided on the endplates 510, 552, the inner member 502, the outer member 504, or any other suitable location along the implant 500. For example, as shown in FIG. 21b showing a close-up side view of the top of the implant 500 when assembled, the inner member 502 may comprise a marking 610 configured to align the first and second series of markings 602, 604. As shown, the marking 610 may be in the form of an arrow. Thus, the number "1" on the endplate 510 is aligned with the arrow marking 610 on the inner member 502, and the opening 544 on the outer member 504, which is configured and dimensioned to receive a portion of an implantation tool. Similarly, as shown in FIG. 21a showing a close-up side view of the bottom of the implant 500 when assembled, the outer member 504 may comprise a marking 612 configured to align the first and second series of markings 602, 604. The marking 612 on the outer member 504 may include a rectangle. The marking 612 may be substantially aligned with the opening 544. As shown, the rectangular marking 612 may be aligned with the arrow 610 on the inner member 502 and the number "1" on endplate 552. Thus, these markings 610, 612 assist in aligning the first and second series of markings 602, 604 together.

One or more additional markings 606, 614 may be provided on the first endplate 510 and one or more additional markings 608 may be provided on the second endplate 552. For example, markings 606 may be interspersed between the series of first markings 602. The markings 606 may be in the form of rectangles which extend along the length of the extension portion 581 of the endplate 510. Marking 614 may be in the form of a square positioned near the distal end 546 of the endplate 510. The markings 606, 614 may help a user to visually identify alignment, for example, between one of the markings 602, marking 610, marking 612, and/or marking 604. Similarly, a marking 608 may be positioned beneath a primary marking 604 to identify the most common alignment between marking 604 for number "1", marking 612, marking 610, and/or marking 602. Any suitable type, number, and position of markings 602, 604, 606, 608, 610, and 612 may be selected to achieve the pre-determined alignment of the implant 500 for a given implantation approach and the desired degree of lordosis or kyphosis.

While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant for engagement between vertebrae, comprising:
   an inner member having a hollow interior portion and an external portion;
   a first endplate having a first surface configured to engage a first vertebral body, the first endplate further having a first extension portion recessed from the first surface and configured to be received by the inner member, wherein the first extension portion contains a first series of markings;
   an outer member having a hollow interior portion configured to coaxially receive the inner member therein, wherein the inner and outer members are moveable relative to each other along a longitudinal axis, wherein the inner member is prevented from translating through an opening at a proximal end of the outer member by a pin that engages a groove in the inner member in a compressed position of the implant, wherein the pin does not engage the groove in an expanded position of the implant;
   a gear member positioned coaxial to the inner member and outer member and axially fixed to the outer member; and
   a second endplate having a second surface configured to engage a second vertebral body, the second endplate further having a second extension portion recessed from the second surface and configured to be received by the outer member, wherein the second extension portion contains a second series of markings,
   wherein at least one of the first and second surfaces include a curvature and at least one of the first and second series of markings are aligned with the curvature,
   wherein when at least one of the first and second series of markings are aligned, the first and second endplates are aligned for a specific approach.

2. The implant of claim 1, wherein the first and second series of markings include alphanumeric characters, numeric characters, colors, symbols, shapes, words, or pictures.

3. The implant of claim 1, wherein the first series of markings includes a plurality of different markings.

4. The implant of claim 1, wherein the second series of markings includes a plurality of different markings which correspond to the first series of markings.

5. The implant of claim 1, wherein a third marking is provided on the inner or outer members to aid in alignment.

6. The implant of claim 1 further comprising a locking member configured to restrict relative movement between the inner member and the outer member, wherein the locking member is configured to be received in the outer member, and wherein the locking member includes an engagement member that engages the gear member to prevent rotation of the gear member.

7. The implant of claim 6, wherein the engagement member engages a cutout formed in the gear member to prevent rotation of the gear member.

8. The implant of claim 1, wherein the gear member includes gear teeth extending around a perimeter of the gear member, the gear teeth extending from a proximal end of the gear member to a distal end of the gear member.

9. An expandable prosthetic implant for engagement between vertebrae, comprising:
   an inner member having a hollow interior portion and an external portion, the inner member comprising a longitudinal groove extending along a length of the inner member;
   a first endplate having a first surface configured to engage a first vertebral body, the first endplate further having a first extension portion recessed from the first surface and configured to be received by the inner member, wherein the first extension portion contains a first series of markings;
   an outer member having a hollow interior portion configured to coaxially receive the inner member therein, wherein the inner and outer members are moveable relative to each other along a longitudinal axis from a first position to a second position;
   a pin having a first end and a second end, the pin extending through the outer member, and the second end configured to engage the groove in the inner member, wherein the pin is disposed outside of the groove in an expanded position of the implant;
   a gear member positioned coaxial to the inner member and outer member and axially fixed to the outer member; and
   a second endplate having a second surface configured to engage a second vertebral body, the second endplate further having a second extension portion recessed from the second surface and configured to be received by the outer member, wherein the second extension portion contains a second series of markings, wherein at least one of the first and second surfaces include a curvature and at least one of the first and second series of markings are aligned with the curvature, wherein when at least one of the first and second series of markings are aligned, the first and second endplates are aligned for a specific approach.

10. The implant of claim 9, wherein the first and second series of markings include alphanumeric characters, numeric characters, colors, symbols, shapes, words, or pictures.

11. The implant of claim 9, wherein the first series of markings includes a plurality of different markings.

12. The implant of claim 9, wherein the second series of markings includes a plurality of different markings which correspond to the first series of markings.

13. The implant of claim 9, wherein a third marking is provided on the inner or outer members to aid in alignment.

14. The implant of claim 9 further comprising a locking member configured to restrict relative movement between the inner member and the outer member, wherein the locking member is configured to be received in the outer member.

15. An expandable prosthetic implant for engagement between vertebrae, comprising:
- an inner member having a hollow interior portion an external portion, the inner member comprising a longitudinal groove extending along a length of the inner member;
- a first endplate having a first surface configured to engage a first vertebral body, the first endplate further having a first extension portion recessed from the first surface and configured to be received by the inner member, wherein the first extension portion contains a first series of markings;
- an outer member having a hollow interior portion configured to coaxially receive the inner member therein, wherein the inner and outer members are moveable relative to each other along a longitudinal axis from a first position to a second position;
- a pin having a first end and a second end, the pin extending through the outer member, and the second end configured to engage the groove in the inner member when the inner and outer members are in the first position and the second end does not engage the groove in the inner member when the inner and outer members are in the second position;
- a gear member position coaxial to the inner member and outer member and axially fixed to the outer member; and
- a second endplate having a second surface configured to engage a second vertebral body, the second endplate further having a second extension portion recessed from the second surface and configured to be received by the outer member, wherein the second extension portion contains a second series of markings,
- wherein at least one of the first and second surfaces include a curvature and at least one of the first and second series of markings are aligned with the curvature,
- wherein when at least one of the first and second series of markings are aligned, the first and second endplates are aligned for a specific approach.

16. The implant of claim 15, wherein a third marking is provided on the inner or outer members to aid in alignment.

* * * * *